(12) United States Patent
González Ferrero et al.

(10) Patent No.: US 10,993,915 B2
(45) Date of Patent: May 4, 2021

(54) MICROPARTICLES FOR ENCAPSULATING PROBIOTICS, OBTAINING SAID MICROPARTICLES AND USES THEREOF

(71) Applicants: UNIVERSIDAD DE NAVARRA, Navarra (ES); CENTRO NACIONAL DE TECNOLOGÍA Y SEGURIDAD ALIMENTARIA, Navarra (ES)

(72) Inventors: Carolina González Ferrero, Navarra (ES); Carlos Javier González Navarro, Navarra (ES); Juan Manuel Irache Garreta, Navarra (ES); Beatriz Marín Calvo, Navarra (ES); Ana Romo Hualde, Navarra (ES); Raquel Virto Resano, Navarra (ES)

(73) Assignees: UNIVERSIDAD DE NAVARRA, Navarra (ES); CENTRO NACIONAL DE TECNOLOGIA Y SEGURIDAD ALIMENTARIA, Navarra (ES)

( * ) Notice: Subject to any disclaimer, the term of this patent is extended or adjusted under 35 U.S.C. 154(b) by 14 days.

(21) Appl. No.: 16/061,551

(22) PCT Filed: Dec. 16, 2016

(86) PCT No.: PCT/EP2016/081385
§ 371 (c)(1),
(2) Date: Jun. 12, 2018

(87) PCT Pub. No.: WO2017/103072
PCT Pub. Date: Jun. 22, 2017

(65) Prior Publication Data
US 2019/0192439 A1 Jun. 27, 2019

(30) Foreign Application Priority Data
Dec. 17, 2015 (EP) .................................... 15382634

(51) Int. Cl.
| | |
|---|---|
| *A23K 10/18* | (2016.01) |
| *A61K 9/16* | (2006.01) |
| *A23L 3/46* | (2006.01) |
| *A23P 10/30* | (2016.01) |
| *A23L 33/135* | (2016.01) |
| *A23L 33/185* | (2016.01) |
| *A23K 20/147* | (2016.01) |
| *A23L 29/294* | (2016.01) |
| *A23L 29/00* | (2016.01) |
| *A23K 40/30* | (2016.01) |
| *A23K 20/24* | (2016.01) |
| *A23L 29/281* | (2016.01) |
| *A23K 40/10* | (2016.01) |
| *A23L 29/20* | (2016.01) |

(Continued)

(52) U.S. Cl.
CPC ............ *A61K 9/1658* (2013.01); *A23K 10/18* (2016.05); *A23K 20/147* (2016.05); *A23K 20/24* (2016.05); *A23K 40/10* (2016.05); *A23K 40/30* (2016.05); *A23L 3/46* (2013.01); *A23L 29/015* (2016.08); *A23L 29/045* (2016.08); *A23L 29/20* (2016.08); *A23L 29/281* (2016.08); *A23L 29/294* (2016.08); *A23L 33/135* (2016.08); *A23L 33/16* (2016.08); *A23L 33/185* (2016.08); *A23P 10/30* (2016.08); *A61K 9/0048* (2013.01); *A61K 9/1611* (2013.01); *A61K 9/1623* (2013.01); *A61K 9/1652* (2013.01); *A61K 9/1694* (2013.01); *A61K 35/745* (2013.01); *A61K 35/747* (2013.01); *A23V 2002/00* (2013.01); *A23Y 2220/17* (2013.01); *A23Y 2220/67* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 9,480,276 | B2 | 11/2016 | Harel et al. |
| 10,111,835 | B2 | 10/2018 | Agueros Bazo et al. |

(Continued)

FOREIGN PATENT DOCUMENTS

| | | | |
|---|---|---|---|
| WO | 2005032568 | A1 | 4/2005 |
| WO | 2008076975 | A1 | 6/2008 |

(Continued)

OTHER PUBLICATIONS

Chen et al. 2009 (Calcium Cross-Linked Soy Protein Beads and Microspheres as Carriers for Nutraceutical Compound Delivery; Chapter 6 in Micro/Nanoencapsulation of Active Food Ingredients ACS Symposium Series: American Chemical Society; Washington DC; pp. 98-115). (Year: 2009).*
Costa et al. 2014 (Immobilization and Microencapsulation of Probiotics; 1st Edition Probiotic Bacteria Fundamentals, Therapy, and Technological Aspects by J. Paulo Sousa e Silva, Ana Cristina Freitas Copyright Year 2014 ISBN 9789814411622 Published Apr. 2, 2014 by Jenny Stanford Publishing; (Year: 2014).*
Maltais et al. 2005 (Formation of Soy Protein Isolate Cold-set Gels: Protein and Salt Effects; Journal of Food Science 70(1): 68-73) (Year: 2005).*

(Continued)

*Primary Examiner* — Mary Maille Lyons
(74) *Attorney, Agent, or Firm* — Tristan A. Fuierer; Olive Law Group, PLLC

(57) ABSTRACT

The invention relates to self-assembling microparticles comprising a solid matrix and probiotic bacteria, wherein the solid matrix comprises soybean protein and a divalent or trivalent metal, and wherein the probiotic bacteria are distributed throughout the solid matrix; said matrix protects said probiotic bacteria during processing, storage, as well as during transit through the gastrointestinal tract, thus prolonging their lifetime and facilitating release into the intestine and improving their probiotic effect. The present invention also relates to the method for obtaining the self-assembling microparticles and to the products and compositions incorporating them.

15 Claims, 14 Drawing Sheets

(51) Int. Cl.
*A61K 9/00* (2006.01)
*A23L 33/16* (2016.01)
*A61K 35/745* (2015.01)
*A61K 35/747* (2015.01)
*A61K 35/00* (2006.01)

(56) References Cited

U.S. PATENT DOCUMENTS

| | | | |
|---|---|---|---|
| 2005/0266069 A1* | 12/2005 | Simmons | A23L 33/135 424/451 |
| 2010/0074994 A1* | 3/2010 | Harel | A23L 3/40 426/61 |
| 2012/0251614 A1* | 10/2012 | Rohwer | A23D 9/00 424/450 |
| 2014/0377409 A1 | 12/2014 | Harel et al. | |

FOREIGN PATENT DOCUMENTS

| | | | |
|---|---|---|---|
| WO | 2014006261 A2 | 1/2014 | |
| WO | WO-2015019307 A1 * | 2/2015 | A61K 2300/00 |

OTHER PUBLICATIONS

Chen et al. 2009 (Chapter 6 in Micro/Nanoencapsulation of Active Food Ingredients ACS Symposium Series: American Chemical Society; Washington DC; pp. 98-115 (Year: 2009).*
Wang et al. 2015 (Encapsulation of Bifidobacterium adolecentis cells with legume proteins and survival under stimulated gastric conditions and during storage in commercial fruit juices; Food Sci. Biotechnol. 24(2):383-391 (Year: 2015).*
Speroni, F., et al.; "Cold-set gelation of high pressure-treated soybean proteins," Food Hydrocolloids, 2013, pp. 85-91, vol. 33.
Maltais, Anne, et al.; "Soy protein cold-set hydrogels as controlled delivery devices for nutraceutical compounds,"Food Hydrocolloids, 2009, pp. 1647-1653, vol. 23.
Antonietti, Markus et al.; "Vesicles and Liposomes: A Self-Assembly Principle Beyond Lipids," Advanced Materials, 2003, pp. 1323-1333, vol. 15.
International Search Report for PCT/EP2016/081385, dated Mar. 14, 2017.
FAO/WHO; "Report of a Joint FAO/WHO Expert Consultation on Evaluation of Health and Nutritional Properties of Probiotics in Food Including Powder Milk with Live Lactic Acid Bacteria," 2001, pp. 1-34.
Dianawati, D., et al; "Survival, Acid and Bile Tolerance, and Surface Hydrophobicity of Microencapsulated *B. animalis* ssp. lactis Bb12 during Storage at Room Temperature," Journal of Food Science, 2011,pp. M592-599, vol. 76.
Krasaekoopt, W. et al.; "The influence of coating materials on some properties of alginate beads and survivability of microencapsulated probiotic bacteria," International Dairy Journal, 2004, pp. 737-743, vol. 14.
Ding, W.K. et al.; "Effect of Various Encapsulating Materials on the Stability of Probiotic Bacteria," Journal of Food Science, 2009, pp. M100-M107, vol. 74.
O'Riordan, K. et al.; "Evaluation of microencapsulation of a Bifidobacterium strain with starch as an approach to prolonging viability during storage," Journal of Applied Microbiology, 2001, pp. 1059-1066, vol. 91.
Heidebach, T. et al.; "Transglutaminase-induced caseinate gelation for the microencapsulation of probiotic cells," International Dairy Journal, 2009, pp. 77-84, vol. 19.
Heidebach, T. et al.; "Influence of casein-based microencapsulation on freeze-drying and storage of probiotic cells," Journal of Food Engineering, 2010, pp. 309-316, vol. 98.

Oliveira et al.; "Stability of microencapsulated B. lactis (BI 01) and L. acidophilus (LAC 4) by complex coacervation followed by spray drying," Journal of Microencapsulation, 2007, pp. 685-693, vol. 24.
Dianawati, D. et al.; "Survival of Bifidobacterium longum 1941 microencapsulated with proteins and sugars after freezing and freeze drying," Food Research International, 2013, pp. 503-509, vol. 51.
Pan et al.; "The aggregation of soy protein isolate on the surface of Bifidobacterium," Food Research International, 2014, pp. 323-328, vol. 64.
Sun et al.; "Preparation and optimization of soy protein isolate-high methoxy pectin microcapsules loaded with Lactobacillus delbrueckii," Food Science & Technology, 2014, pp. 1287-1293, vol. 49.
FAO/WHO; "Guidelines for the Evaluation of Probiotics in Food," 2002, pp. 1-11.
K.H. Lee et al.; "Protein Solubility Characteristics of Commercial Soy Protein Products," JAOCS, 2003, vol. 80, pp. 85-90.
Bao et al.; "Screening of potential probiotic properties of Lactobacillus fermentum isolated from tradition dairy products," Food Control, 2010, pp. 695-701, vol. 21.
International Search Report, dated Mar. 14, 2017.
FAO/WHO. Report of a Joint FAO/WHO Expert Consultation on Evaluation of Health and Nutritional Properties of Probiotics in Food Including Powder Milk with Live Lactic Acid Bacteria, Córdoba, Argentina 2001.
Dianawati, D. et al, "Survival, Acid and Bile Tolerance, and Surface Hydrophobicity of Microencapsulated *B. animalis* ssp. lactis Bb 12 during Storage at Room Temperature," Journal of Food Science, 2011, 76(9), M592-599.
Krasaekoopt, W. et al., "The influence of coating materials on some properties of alginate beads and survivability of microencapsulated probiotic bacteria," International Dairy Journal, 2004, 14(8), 737-743.
Ding, W.K. et al., "Effect of Various Encapsulating Materials on the Stability of Probiotic Bacteria," Journal of Food Science, 2009, 74(2), M100-M107.
O'Riordan, K. et al., "Evaluation of microencapsulation of a Bifidobacterium strain with starch as an approach to prolonging viability during storage," Journal of Applied Microbiology, 2001, 91, 1059-1066.
Heidebach, T. et al., "Transglutaminase-induced caseinate gelation for the microencapsulation of probiotic cells," International Dairy Journal, 2009, 19, 77-84.
Heidebach et al., "Influence of casein-based microencapsulation on freeze-drying and storage of probiotic cells," Journal of Food Engineering, 2010, 98, 309-316.
Oliveira et al., "Stability of microencapsulated B. lactis (BI 01) and L. acidophilus (LAC 4) by complex coacervation followed by spray drying," Journal of Microencapsulation, 2007, 24, 685-93.
Dianawati, D. et al., "Survival of Bifidobacterium longum 1941 microencapsulated with proteins and sugars after freezing and freeze drying," Food Research International, 2013, 51, 503-509.
Pan et al., "The aggregation of soy protein isolate on the surface of Bifidobacterium," Food Research International, 2014, 64, 323-328.
Sun et al., "Preparation and optimization of soy protein isolate-high methoxy pectin microcapsules loaded with Lactobacillus delbrueckii," Food Science & Technology, 2014, 49, 1287-1293.
Bao et al., "Screening of potenional probiotic properties of Lactobacillus fermentum isolated from traditional dairy products," Food Control, 2010, 21 (5): 695-701.
K. H. Lee et al, "Protein Solubility Characteristics of Commercial Soy Protein Products," JAOCS, vol. 80, 2003, 85-90.
FAO/WHO 2002. "Guidelines for the evaluation of probiotics in food," London.

* cited by examiner (a)      (b)

(c)      (d)

(a)

(b)

(a)

(b)

MICROPARTICLES FOR ENCAPSULATING PROBIOTICS, OBTAINING SAID MICROPARTICLES AND USES THEREOF

CROSS-REFERENCE TO RELATED APPLICATIONS

This application is filed under the provisions of 35 U.S.C. § 371 and claims the priority of International Patent Application No. PCT/EP2016/081385 filed on 16 Dec. 2016 entitled "MICROPARTICLES FOR ENCAPSULATING PROBIOTICS, OBTAINING SAID MICROPARTICLES AND USES THEREOF" in the name of Carolina GONZALEZ FERRERO, et al., which claims priority to European Patent Application No. 15382634.2, filed on 17 Dec. 2015, both of which are hereby incorporated by reference herein in their entirety.

FIELD OF THE INVENTION

The present invention is comprised in the scope of food, nutraceutical, cosmeceutical and pharmaceutical technology. Particularly, it relates to microparticles comprising a solid matrix of soybean protein and probiotic bacteria, to a method for obtaining the microparticles and to their applications.

BACKGROUND OF THE INVENTION

The intestinal microbiota of a healthy adult is relatively stable and contains various beneficial bacterial populations made up primarily of *Lactobacillus* and *Bifidobacterium* species playing an important role in host health. Beneficial colonic microbiota imbalance can contribute to the development of different disorders, such as gastrointestinal tract infections, constipation, irritable bowel syndrome, inflammatory bowel disease, allergies, heart diseases and colon cancer. The World Health Organization (WHO) has recommended the use of the therapeutic and prophylactic potential of beneficial microorganisms or probiotics to prevent these risks.

Probiotics are defined as live microorganisms which provide health benefit on the host when administered in adequate amounts (FAO/WHO. Report of a Joint FAO/WHO Expert Consultation on Evaluation of Health and Nutritional Properties of Probiotics in Food Including Powder Milk with Live Lactic Acid Bacteria, Córdoba, Argentina 2001). Several studies have reported the beneficial effects of probiotics on human health, including reduction of lactose intolerance, resistance to enteric pathogens, prevention of cancer, cardiovascular diseases and gastrointestinal disorders, and modulation of host immune response. Additionally, the possible role of probiotics in dental caries prevention is under research.

Probiotics exhibit their beneficial effects when they are alive and contain an adequate number of bacteria. A daily dose of at least $10^6$-$10^7$ living cells has been suggested to assure health-relevant effects following the consumption of probiotic products.

There are four basic ways for consuming probiotics: as a concentrated culture added to a drink (e.g., fruit juice, etc.), inoculated in prebiotic fibers, as a dietary supplement in lyophilized cell dosage forms (e.g., powder, capsules, tablets, etc.) and inoculated in milk-based foods.

However, probiotics, such as those belonging to the genus of *Lactobacillus*, face challenges from the extreme gastrointestinal environment which reduces the survival rate of the probiotics reaching the small intestine. To overcome these problems, many methods have been developed to protect the probiotics from being destroyed, such as drying techniques or microencapsulation.

Spray-drying has been used for the preservation of probiotic bacteria due to the easy availability of the process as well as to low cost, however, it gives rise to a high bacterial mortality rate as a result of the simultaneous dehydration and thermal inactivation process of the microorganisms.

Microencapsulation is considered the preferred method as it allows bacteria to be entrapped or contained in microcapsules, protecting them from the acidic environment of the stomach and from the destructive effects of bile fluid in the upper part of the intestine. In consideration of these conditions, bowel soluble microcapsules must be resistant to pH levels in the range of 1.0 to 3.0 in the gastric fluid and then disintegrate in the duodenum or the first half of the small intestine.

Methods of encapsulation include chemical, physical and mechanical processes, such as interfacial polymerization, in situ polymerization, chemical radiation, coacervation and extrusion.

The materials used for microencapsulation are typically natural polysaccharides and proteins because they often lack cytotoxicity and have safe biodegradation products and they do not require the use of organic solvents for preparing microcapsules. Alginate-based microencapsulation has been widely described to test the bacterial survival in acidic and bile conditions, but some studies revealed that alginate was not always successful as a protectant of probiotic bacteria (Dianawati, D. et al, *Journal of Food Science*, 2011, 76(9), M592-599; Krasaekoopt, W. et al., *International Dairy Journal*, 2004, 14(8), 737-743).

The use of carbohydrates, such as guar gum, locust beam gum or waxy maize starch was also not effective in protecting probiotic bacteria upon exposure to very low pH (Ding, W. K. et al., *Journal of Food Science*, 2009, 74(2), M100-M107; O'Riordan, K. et al., *Journal of Applied Microbiology*, 2001, 91, 1059-1066).

Over the past few years, proteins, as novel wall materials, have become a popular choice for the encapsulation of probiotics.

One of the proteins used for encapsulating probiotic bacteria is casein, a conjugated protein making up about 80% of total milk proteins. Studies have been developed using this protein alone or in combination with other polymers, including polysaccharides, for encapsulating probiotic bacteria (Heidebach, T. et al., *International Dairy Journal*, 2009, 19, 77-84; Heidebach et al., *Journal of Food Engineering*, 2010, 98, 309-316; Oliveira et al., *Journal of Microencapsulation*, 2007, 24, 673-81). Good encapsulation efficiency results were being obtained without compromising bacterial viability. Studies on the resistance to acidic pH conducted in the three identified papers clearly show that the microcapsules protect the bacteria from acidity. However, none of said papers conducts the study using pepsin to reproduce the actual gastric conditions which are more aggressive than mere acidic pH (the enzyme may degrade the protein and increase the bacterial exposure to the medium). Only a significant improvement in the protection of the probiotic bacteria from being inactivated by external agents during processing and storage and from the acidic-peptidic conditions of the upper gastrointestinal tract has been obtained when combining casein with chitosan as microparticles-forming material (WO2014/006261).

Soybean protein has also been used to encapsulate probiotics. Dianawati, D. et al. (*Food Research International*, 2013, 51, 503-509) describes the microencapsulation of *Bifidobacterium longum* by means of a w/o emulsion followed by pasteurization, incorporation of bacteria and freeze-drying. A combination of a protein, such as sodium caseinate, whey protein concentrate, soybean protein isolate or skim milk with sugars (glycerol, mannitol or maltodextrin) was used as microcapsule-forming materials, stating that milk proteins are more effective than soybean protein isolate.

The protecting mechanism of soybean protein isolate (SPI) on *Bifidobacterium* has been studied by Pan et al. (*Food Research International*, 2014, 64, 323-328) in a system wherein *Bifidobacterium longum* is localized in the microcapsule core and SPI acts as a wall-coating material. The use of SPI is postulated as a food ingredient in protecting probiotics but no data regarding the stability under storage or gastrointestinal resistance have been provided.

Sun et al. (*Food Science & Technology*, 2014, 49, 1287-1293) describe the use of SPI with high methoxy pectin (HMP) as encapsulating materials for probiotic bacteria stating that the complex SPI:HMP with a particular volume ratio 7:1 can increase the number of alive bacteria when compared to naked bacteria.

Document WO2008/076975 discloses the preparation of a cross-linked gel based on a polysaccharide and a protein, such as soybean protein, which is further lyophilized, ground and sieved to form a dried microsized structure to protect probiotic bacteria from high temperatures and humidity conditions.

WO2005/032568 describes a powdery fermented product obtained by fermenting soy milk in the presence of lactic acid bacteria and yeast, neutralizing the fermented liquid product obtained with a calcium compound, and subsequent drying and pulverization to give the fermented product in powder form.

Cold-set particulate hydrogels made from soy protein have also been described in the prior art to incorporate heat-labile compounds or probiotics during the gelation step (Speroni, F. et al., *Food Hydrocolloids*, 2013, 33, 85-91) and as controlled delivery devices for nutraceutical compounds such as riboflavin (Maltais, A., Food Hydrocolloids, 2009, 23, 1647-53). These hydrogels are obtained by denaturing the soy protein and subsequent re-arrangement in a three-dimensional network stabilized by non-covalent interactions, with calcium ions interspersed within the denatured protein structure. However, it should be pointed out that said hydrogels may not be considered in any case as comprising individual microparticles of a solid self-assembling soybean-containing matrix.

In spite of the encapsulating systems described in the prior art, the benefits obtained can still be improved and therefore, there is still a need to develop systems which enhance the protection of the probiotic bacteria through the gastrointestinal tract that can be obtained by means of easily available processes and thus be implemented at industrial scale.

SUMMARY OF THE INVENTION

The inventors of the present invention have discovered microparticles having the capacity of encapsulating probiotic bacteria by means of an entrapment mechanism, for their subsequent incorporation into foods and nutraceutical, cosmeceutical and pharmaceutical products. These microparticles protect the probiotic bacteria from being inactivated by external agents when processing the food or nutraceutical, cosmeceutical or pharmaceutical product in which they are incorporated, but also during storage over long periods under environmental or controlled conditions, increasing the shelf life of these products when compared, for example, to lyophilized or spray-dried bacteria. Furthermore, after being administered to the human or animal body, they facilitate probiotic bacteria release in the desired location, and improve their protection from the "acidic-peptic" conditions of the upper gastrointestinal tract, particularly of the stomach, when compared to naked or lyophilized probiotic bacteria as pointed out in the experimental part of this document.

These microparticles are stable and inert in the food or in the nutraceutical, cosmeceutical or pharmaceutical formulation in which they are incorporated, preventing the food, nutraceutical, cosmeceutical or pharmaceutical matrix from compromising the bacterial viability.

The microparticles have the additional advantage of being safe for people having milk protein allergy, thus offering a commercial alternative to other microparticles, such as those made with casein.

Furthermore, the inventors have developed a method for obtaining these microparticles in a simple manner, particularly by a method of simple coacervation, which is applicable at industrial scale. This method does not include the use of surfactants or emulsifiers, synthetic polymers, or any reagent which is not approved as food additive.

Furthermore, this process allows microparticles to be spontaneously formed in the medium in which they are obtained by means of local interactions of the different components thereof, thus leading to a uniform dispersion of self-assembling microparticles having a matrix-type structure wherein probiotic are distributed.

The microparticles can be resuspended, but not dissolved, easily in an aqueous medium, protecting the probiotic bacteria they contain from the medium. The microparticles of the invention remain stable in the product in which they are incorporated, so a significant decrease in the viable bacteria count after long storage periods under environmental and/or controlled conditions is prevented. Furthermore, these microparticles are applicable to different types of foods, from drinks and dairy products to solid foods, and in nutraceutical products. Likewise, said microparticles can be formulated into cosmeceutical and pharmaceutical formulations.

The microparticles of the invention provide a new system for entrapping and stabilizing probiotic microorganisms. According to the present invention, a solid matrix comprising soybean protein in combination with a di- or tri-valent metal is used as a vehicle for protecting the probiotic bacteria from the environmental conditions during long storage periods and from the gastric conditions, thus increasing the lifetime and facilitating release into the intestine and improving their probiotic effect. Furthermore, the soybean protein per se has significant nutritional properties complementing the beneficial effects of the entrapped probiotic bacteria itself.

Therefore, a first aspect of the present invention relates to self-assembling microparticles comprising a solid matrix and probiotic bacteria, wherein the solid matrix comprises soybean protein and a di- or tri-valent metal cation, and wherein the probiotic bacteria are distributed throughout the solid matrix. Preferably, the probiotic bacteria are homogeneously distributed throughout said solid matrix.

In another aspect, the invention relates to a method for obtaining the self-assembling microparticles provided by this invention, which comprises:

a) preparing a dispersion of soybean protein in an alkaline aqueous solution;
b) preparing a suspension of probiotic bacteria;
c) mixing the suspension of the probiotic bacteria prepared in step b) with the dispersion of soybean protein prepared in step a);
d) adding to the resulting mixture obtained in step c) a di-valent or tri-valent metal cation.

In another aspect, the invention also relates to self-assembling microparticles obtainable by the process as described above.

Another aspect of the invention relates to a composition comprising at least one self-assembling microparticle provided by this invention, or at least one self-assembling microparticle obtainable by the process provided by this invention.

In another aspect, the invention relates to a food, nutraceutical, cosmeceutical or pharmaceutical product comprising i) at least one self-assembling microparticle provided by this invention and/or a self-assembling microparticle obtained by means of the method of the invention, or ii) a composition provided by this invention.

DETAILED DESCRIPTION OF THE INVENTION

Figure 1:
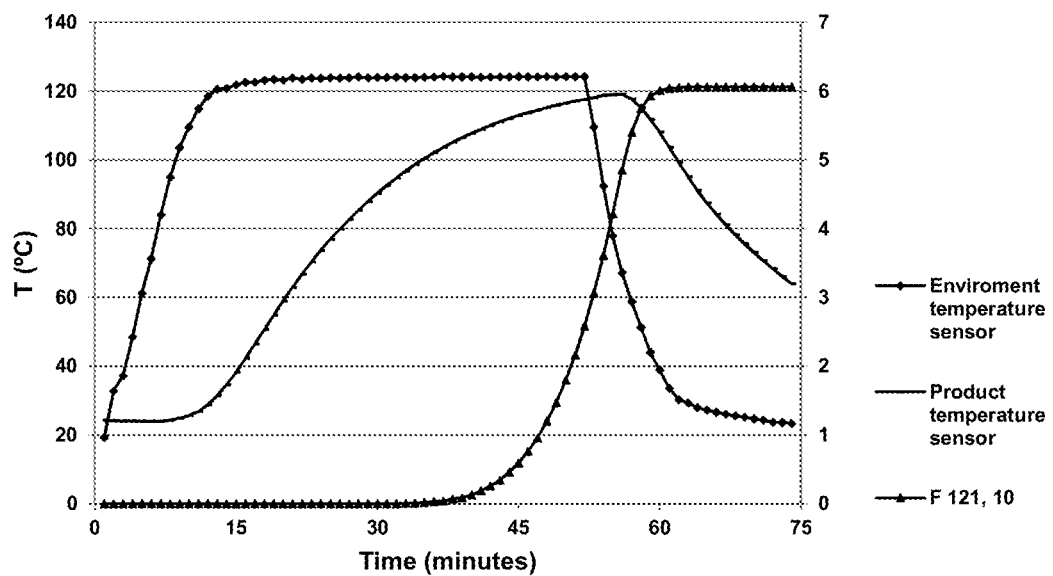
FIG. 1 is a graph of the heat treatment of sterilization applied to soybean flour in a rotary autoclave, where diamond graph shows the environment temperature sensor, horizontal rectangles show the product temperature sensor and triangles indicate the amount of heat treatment delivered at 121° C. per minute over ten minutes)($F_{121}^{10}$).

The present invention relates to the production of microparticles for encapsulating or entrapping probiotic bacteria, for the purpose of preventing their inactivation after incorporation into food, nutraceutical, pharmaceutical or cosmeceutical matrices and of protecting them from the "acidic-peptic" conditions during transit through the gastrointestinal tract once they have been administered.

Microparticles of the Invention

A first aspect of the present invention relates to self-assembling microparticles, hereinafter "microparticles of the invention", comprising a solid matrix and probiotic bacteria, wherein the solid matrix comprises soybean protein and a di- or tri-valent metal cation, and wherein the probiotic bacteria are distributed throughout the solid matrix. More preferably, the probiotic bacteria are homogeneously distributed throughout the solid matrix.

As used herein, the term "microparticles" is used to designate colloidal systems having spherical or quasi-spherical shape and having a mean size less than 1 millimeter (mm), generally ranging from 0.5 to 999 micrometers (μm), typically ranging from 1 to 900 μm. In a particular embodiment, the microparticles of the invention have a size less than 1 mm, generally comprised between 0.1 and 999 μm, typically between 0.2 and 900 μm, advantageously between 0.3 and 500 μm, preferably between 0.4 and 250 μm, more preferably between 0.5 and 125 μm, even more preferably between 0.7 and 50 μm, still more preferably between 1 and 30 μm, even still more preferably between 5 and 15 μm. "Mean size" is understood as the average diameter of the microparticle population, moving together in an aqueous medium. The mean size of these systems can be measured by standard methods known by the person skilled in the art and are described, for example, in the experimental part below.

In contrast to other microparticles containing soybean protein, metal cation and probiotic bacteria, such as those described in WO2008/076975, which basically correspond to irregular crystals obtained from lyophilization, grinding and sieving a gel previously formed, the microparticles of the invention are further characterized for being self-assembling microparticles, understanding as such microparticles as defined above having an organized structure or pattern resulting from the local interactions among the components of microparticles themselves.

Thus, in the scope of the present invention, the microparticles of the present invention can be considered as comprising building blocks re-engineered from natural soybean protein which, in the presence of di- or tri-valent metal cation, self-assemble to form solid matrix systems. During the assembly process, bacteria are captured by means of an entrapment mechanism, being distributed throughout the entire matrix.

Therefore, the term "solid matrix" refers to a solid microsphere having a matrix-type structure in which the soybean protein and the di- or tri-valent metal cation form a continuous structure and wherein the probiotic bacteria are distributed, preferably homogeneously distributed, throughout the entire matrix.

Thus, contrary to the term "capsule" or "microcapsule", the solid matrix of the microparticles of the invention has not differentiated external and internal structures and, therefore, the probiotic bacteria are distributed, more preferably homogeneously distributed, throughout the entire matrix forming the microparticle and not encapsulated or confined within a central cavity thereof.

As used herein, the term "soybean protein" includes whole soy milk, defatted concentrated soy milk, concentrated soybean protein, extracted soybean protein, isolated soybean protein, soybean protein fractions, etc. Such soybean proteins are different from each other in the contents of proteins, form, properties and functions for each of products.

Soybean milk can be produced as a first soybean protein by subjecting soybeans to solvent extraction to separate them into rind and soybean oil, pulverizing the residual skimmed soybeans under heating to prepare powdered skimmed soybeans, and removing fibrous non-soluble products. Alternatively, soybean milk can be produced as a first soybean protein by subjecting soybeans to solvent extraction to separate them into rind and soybean oil, boiling the residual skimmed soybeans to prepare a water solution containing swollen soybeans through water-extraction and removing fibrous non-soluble products.

Soybean proteins can also be produced by sterilizing soybean milk under drying to prepare dried soybean milk.

The soybean protein used in the present invention may be a powdery soybean protein product prepared from defatted soybean flour by a variety of art-recognized methods, which can increase the protein content. Specific examples thereof include extracted soybean protein having a soybean protein content ranging from 50 to 60 wt %, concentrated soybean protein having a soybean protein content ranging from 60 to 70 wt %, soybean protein fraction having a soybean protein content ranging from 70 to 80 wt %, and isolated soybean protein having a soybean protein content of not less than 90 wt %.

In a particular embodiment, isolated soybean protein products are preferred because of their high soybean protein contents. Alternatively, it is also possible to use the foregoing soybean protein products slightly hydrolyzed to such an extent that they do not have extreme bitterness and rough taste.

In another particular embodiment, the soybean protein used in the present invention is preferably a soybean protein fraction obtained from soybean flour, a by-product in the production of soybean milk. More particularly, the soybean protein fraction has a soybean protein content ranging from 70 to 80 wt %. The soybean protein obtained from the residue of soy flour not only improves the viability of probiotic microorganisms, but also provides a value to the by-product originated in the soybean milk processing.

The conventional procedure for the production of isolated soybean protein and soybean protein fractions is based on protein solubilization at neutral or slightly alkaline pH, and precipitation by acidification to the isoelectric region, near pH 4.5. The resulting isoelectric product is subsequently subjected to spray-drying or freeze-drying to obtain the product in powder form.

The soybean protein may also be in form of soybean proteinates which can be produced by resuspending the resulting isoelectric product as that mentioned above in water, neutralizing with different bases and spray-drying or freeze-drying the resulting solution or suspension. Depending on the base used for neutralization, sodium, potassium, ammonium or calcium soybean proteinates can be produced.

Since spray-drying or freeze-drying are the common drying methods in the production of concentrated soybean protein, extracted soybean protein, isolated soybean protein and soybean protein fractions, the primary physical form thereof is that of fine powders. However, the soybean protein can be in the form of soybean protein curds, particle-like separated soybean proteins, particle-like concentrated soybean proteins, spun fiber-like soybean proteins, structural fiber-like soybean proteins, particle-like soybean proteins, hunk-like soybean proteins, flake-like soybean proteins, bar-like soybean proteins, dice-like soybean proteins, which are made by further processing.

Soybean protein curds can be produced by separating proteins from the soybean milk by acid. Particle-like separated soybean proteins can be produced by sterilizing soybean protein curds, neutralizing them, and subjecting them to spray drying. Soybean protein curds can be produced by washing the above-described skimmed soybeans with acid or alcohol. Particle-like concentrated soybean proteins can be produced by sterilizing soybean protein curds, neutralizing them, and subjecting them to spray drying. Soybean protein curds, particle-like separated soybean proteins, particle-like concentrated soybean proteins produced in such a manner as described above are processed by means of a single-screw extruder, nozzle spraying, or double-screw extruder to form spun fiber-like soybean proteins, structural fiber-like soybean proteins, particle-like soybean proteins, hunk-like soybean proteins, flake-like soybean proteins, bar-like soybean proteins, dice-like soybean proteins.

The solid matrix comprised in the microparticles of the invention also contains at least a divalent metal cation, at least a trivalent metal cation or a combination thereof.

As used herein, the term "divalent metal cation" refers to a cation originating from any metal element the valence of which is 2, for example, an alkaline earth-metal, e.g., calcium, magnesium, zinc, etc., or if it has several valences, one of them is 2, for example, iron, etc., provided that said cation is pharmaceutically acceptable or suitable for use in food. In a preferred embodiment, the divalent metal cation is selected from $ca^{2+}$, $Mg^{2+}$, $Zn^{2+}$ and $F^{2+}$ and combinations thereof, more preferably is $Ca^{2+}$.

As used herein, the term "trivalent metal cation" refers to a cation originating from any metal element the valence of which is 3, or if it has several valences, one of them is 3, for example, iron, etc., provided that said cation is pharmaceutically acceptable or suitable for use in human or animal food.

As will be understood by the person skilled in the art, the di-valent or tri-valent metal can be provided by any suitable source of said metal cation, such as a compound which gives rise to said di- or tri-valent metal cation in an aqueous solution. For example, in the case of using $Ca^{2+}$, this divalent metal cation can be obtained from calcium chloride, calcium acetate, calcium gluconate, calcium lactate, calcium sorbate, calcium ascorbate, calcium citrate, calcium propionate, calcium sulfate, etc., or mixtures of said compounds.

In a particular embodiment of the invention, the by weight ratio of the soybean protein and the di- or tri-valent metal cation varies within a wide range from 1:1 to 100:1 which confers microparticles with a regular morphology, namely a uniform and spherical shape, in contrast to a fusiform morphology obtained when higher ratios are used, as pointed out in the experimental part below. More preferably, the by weight ratio of the soybean protein and the di- or tri-valent metal cation varies from 2:1 to 80:1, even more preferably from 5:1 to 60:1, most preferably from 10:1 to 40:1.

In another preferred embodiment, the metal cation is a divalent metal cation, more preferably $Ca^{2+}$.

More particularly, the by weight ratio of the soybean protein and calcium cation ($C^{2+}$) varies within a wide range from 5:1 to 60:1, more preferably from 10:1 to 40:1.

As mentioned herein before, the microparticle of the invention comprises probiotic bacteria which are distributed, more preferably homogeneously distributed, throughout the entire solid matrix formed by the soybean protein and the di- or tri-valent metal cation. Thus, said probiotic bacteria are not encapsulated or confined in the central cavity of the microparticle as the solid matrix is formed by a solid microsphere in which the soybean protein and the di- or tri-valent metal form a solid continuous structure.

As used herein, the term "probiotic" is defined as a live microorganism which exerts a beneficial physiological action on host health when administered in suitable amounts (FAO/WHO 2002. Guidelines for the evaluation of probiotics in food, London). The probiotics used in the present invention are "probioticbacteria", i.e., live bacteria which exert a beneficial physiological action on host health when administered in suitable amounts. In a particular embodiment, said probiotic bacteria are bacteria of the genus *Bifidobacterium* or *Lactobacillus*. In a more particular embodiment, said probiotic bacteria are selected from *L. plantarum* and *L. casei*. In a specific embodiment, the probiotic bacteria are *L. plantarum* CECT 220 and *L. casei* CECT 475 isolated from corn silage and cheese, respectively. In another particular embodiment, said probiotic bacteria are a strain of *Bifidobacterium animalis* subsp. *Lactis*, such as those marketed under the trademark BB-12®.

The amount of probiotic bacteria per unit of weight of the matrix that may be present in the microparticles of the invention can vary within a wide range, nevertheless, in a particular embodiment, the microparticles of the invention comprise at least $10^6$ colony forming units per gram (CFU/g) of matrix, generally between $10^6$ CFU/g and $5 \times 10^{13}$ CFU/g, preferably between 10' CFU/g and $10^{12}$ CFU/g.

In another particular and optional embodiment, the microparticles of the invention further comprise a compound protecting the matrix and the probiotic bacteria during the process of drying the microparticles, or of drying the suspension containing the microparticles of the invention by means of conventional methods, for example, by means of spray drying, hereinafter, "protecting agent". Said protecting agent does not form part of the solid matrix of the microparticles but acts as a bulking agent to facilitate the drying of microparticles in an efficient way, so as the structure thereof is maintained and the probiotic bacteria withstand the thermal conditions. Virtually, any compound complying with those characteristics can be used as a protecting agent. In a particular embodiment, said protecting agent is a saccharide or generally a suitable food additive which, in addition to the protective role, acts as a prebiotic. As used herein, the term "prebiotic" refers to a non-digestible food ingredient which stimulates probiotic growth and/or activity. Non-limiting, illustrative examples of protecting agents which can be used within the context of the present invention include lactose, mannitol, sucrose, maltodextrin, glucose, sorbitol, etc., as well as substances with prebiotic characteristics, such as for example, oligofructose, pectin, inulin, oligosaccharides (e.g. galacto-oligosaccharides, human milk oligosaccharides), lactulose, dietary fiber, etc., and any combination thereof. In a particular embodiment, the protecting agent is selected from maltodextrin, inulin, fructooligosaccharides and combinations thereof. If the microparticles of the invention include a protecting agent, the by weight ratio of the matrix and the protecting agent can vary within a wide range; nevertheless, in a particular embodiment, the soybean protein:protecting agent by weight ratio is 1:0.1-5, typically 1:0.5-4, preferably about 1:1.

In another particular embodiment, the microparticles of the invention are devoid of any coating material. Thus, said microparticles comprise the solid matrix as described above and probiotic bacteria and no coating layer/material coats or encases the solid matrix. In this particular embodiment, the solid matrix comprises soybean protein and a di- or tri-valent metal cation and the probiotic bacteria are distributed, more preferably homogeneously distributed, throughout the solid matrix.

In another particular embodiment, the self-assembling microparticles of the invention consist of a solid matrix and probiotic bacteria, wherein the solid matrix comprises soybean protein and a di- or tri-valent metal cation, and wherein the probiotic bacteria are distributed throughout the solid matrix. More preferably, the probiotic bacteria are homogeneously distributed throughout the solid matrix.

In this particular embodiment, it is preferred that the weight ratio of the soybean protein and the di- or tri-valent metal cation varies within a range from 1:1 to 100:1, more preferably from 2:1 to 80:1, even more preferably from 5:1 to 60:1, most preferably from 10:1 to 40:1.

It is also preferred that the metal cation is a divalent metal cation, more preferably $Ca^{2+}$. More particularly, the by weight ratio of the soybean protein and calcium cation ($Ca^{2+}$) varies within a wide range from 5:1 to 60:1, more preferably from 10:1 to 40:1.

In another particular embodiment, the self-assembling microparticles of the invention consist of a solid matrix and probiotic bacteria, wherein the solid matrix consists of soybean protein and a di- or tri-valent metal cation, and wherein the probiotic bacteria are distributed throughout the solid matrix. More preferably, the probiotic bacteria are homogeneously distributed throughout the solid matrix.

In this particular embodiment, it is preferred that the weight ratio of the soybean protein and the di- or tri-valent metal cation varies within a range from 1:1 to 100:1, more preferably from 2:1 to 80:1, even more preferably from 5:1 to 60:1, most preferably from 10:1 to 40:1.

It is also preferred that the metal cation is a divalent metal cation, more preferably $Ca^{2+}$. More particularly, the by weight ratio of the soybean protein and calcium cation ($Ca^{2+}$) varies within a wide range from 5:1 to 60:1, more preferably from 10:1 to 40:1.

Method for Obtaining the Microparticles of the Invention

Another aspect of the present invention refers to a process, hereinafter "process of the invention", for obtaining the self-assembling microparticles as those described above.

Said process comprises:
a) preparing a dispersion of soybean protein in an alkaline aqueous solution;
b) preparing a suspension of probiotic bacteria;
c) mixing the suspension of the probiotic bacteria prepared in step b) with the dispersion of soybean protein prepared in step a);
d) adding to the resulting mixture obtained in step c) a di-valent or tri-valent metal cation.

Step a) of the process of the invention provides a dispersion of soybean protein in an alkaline aqueous solution.

The soybean protein may have different origin, for example it may be a concentrated soybean protein, extracted soybean protein, isolated soybean protein, soybean protein fractions, etc. Methods for obtaining soybean protein are described herein above.

In a preferred embodiment, the soybean protein is isolated soybean protein or a soybean protein fraction obtained from soybean flour by means of any of the methods described herein above.

In a particular embodiment, the soybean protein is in the form of proteinates, for example sodium, potassium, ammonium or calcium soybean proteinates.

The dispersion of the soybean protein in the alkaline aqueous solution can be obtained by conventional methods known by those skilled in the art, for example by adding the soybean protein to the alkaline aqueous solution.

In a particular embodiment, the alkaline aqueous solution is a buffered solution having a pH ranging from 9 to 12, more preferably about 10. Preferably, said alkaline buffered solution is an aqueous carbonate solution.

The amount of soybean protein that can be added to the alkaline aqueous solution can vary within a wide range, nevertheless, in a particular embodiment, the amount dispersed in said alkaline aqueous solution is comprised between 0.5% and 15% (w/v), preferably between 1% and 10% (w/v), even more preferably between 1% and 5% (w/v). Said dispersion of soybean protein preferably does not contain any organic solvent.

In a preferred embodiment, the dispersion of soybean protein is subjected to homogenization by means, for example, of stirring, and to a subsequent centrifugal process in order to collect the supernatant.

The process of the invention further comprises the preparation of a suspension of probiotic bacteria. Although virtually any probiotic bacteria can be used, in a particular embodiment, said probiotic bacteria are bacteria of the genus *Bifidobacterium* or *Lactobacillus*. In a more particular embodiment, said probiotic bacteria are *L. plantarum* or *L. casei*. In a specific embodiment, the probiotic bacteria are *L. plantarum* CECT 220 and *L. casei* CECT 475. In another particular embodiment, said probiotic bacteria are a strain of *Bifidobacterium animalis* subsp. *lactis*, such as that marketed under the trademark BB-12®.

The bacterial suspension comprises, in addition to the probiotic bacteria, a medium suitable for the corresponding probiotic bacteria. Said media are known by the persons skilled in the art. In a particular embodiment, when said probiotics are bacteria of the genus *Lactobacillus*, for example, *L. plantarum* or *L. casei*, said medium comprises broth for *Lactobacillus* according to De Man, Rogosa and Sharpe, such as that identified as 110661 MRS broth (Merck) [MRS broth]; said medium allows lactobacilli and other lactic acid bacteria to grow well and is commonly used for culturing and enriching lactobacilli from clinical samples and foods, particularly dairy products. Generally, the MRS medium comprises (in g/L): 10 g polypeptone; 10 g meat extract, 5 g yeast extract, 20 g glucose, 1.08 ml Tween® 80 (polyethoxylated sorbitan monooleate or polysorbate 80), 2 g potassium phosphate, 5 g sodium acetate, 2 g ammonium citrate, 0.2 g magnesium sulfate, 0.05 g manganese sulfate. The pH of the medium at a temperature of 25° C. is 6.4±0.2. This culture medium allows abundant development of all lactobacillus species. Peptone and glucose are the source of nitrogen, carbon and other elements necessary for bacterial growth. The polyethoxylated sorbitan monooleate, magnesium, manganese and acetate provide co-factors and can inhibit the development of some microorganisms. Ammonium citrate acts as an inhibitory agent inhibiting the growth of Gram negative bacteria.

The amount of probiotic bacteria which may present in the bacterial suspension can vary within a wide range; nevertheless, in a particular embodiment, the amount of probiotic bacteria present in the bacterial suspension is at least $10^6$ CFU/ml, generally between $10^6$ and $5\times10^{12}$ CFU/ml, preferably between 10' and $10^{12}$ CFU/ml.

In a particular embodiment, once the bacteria have been cultured in the culture medium until early stationary phase growth, the bacterial suspension is subjected to centrifugation in order to eliminate the culture medium. Then, the bacteria are washed to remove any metabolite that would have been formed as well as residues of the culture medium. The washed bacteria are resuspended in an aqueous solution containing a saccharide, such as sucrose, sucralose or other suitable disaccharide, such as for example, maltose or trehalose. If said bacterial suspension contains a disaccharide, for example, a sucrose, the amount of disaccharide (e.g., sucrose) present in said bacterial suspension will be comprised between 0.1% and 10% (w/v) of disaccharide (e.g., sucrose), preferably between 1% and 3% (w/v).

Once the dispersion of soybean protein and the suspension of probiotic bacteria are prepared, they are mixed according to step c) of the process of the invention. When the dispersion of soybean protein prepared according to step a) is subjected to homogenization and centrifugal process, it is the supernatant which is mixed with the suspension of probiotic bacteria.

The soybean protein and the probiotic bacteria are preferably mixed at room temperature, i.e., at a temperature comprised between 18° C. and 25° C., preferably between 20° C. and 22° C., so as to not affect the viability of the probiotic bacteria, advantageously under stirring.

As mentioned before, the matrix comprised in the nanoparticles of the invention further comprises a di- or tri-valent metal cation which is pharmaceutically acceptable or suitable for use in human or animal food.

Thus, the process of the invention further comprises the addition of a di- or tri-valent metal cation to the mixture containing soybean protein and probiotic bacteria. In a particular embodiment, the di- or tri-valent metal cation can be added to said mixture in the form of an aqueous solution. The di- or tri-valent metal cation can be provided by any suitable source of said cation, such as a compound which gives rise to said di- or tri-valent cation in an aqueous solution. In a preferred embodiment, the cation is a di-valent metal cation, more preferably said cation is selected from $Ca^{2+}$, $Mg^{2+}$, $Zn^{2+}$ and $Fe^{2+}$, even more preferably the cation is $Ca^{2+}$. The calcium cation can be provided by an aqueous solution of calcium chloride, calcium acetate, calcium gluconate, calcium lactate, calcium sorbate, calcium ascorbate, calcium citrate, calcium propionate, calcium sulfate, etc., or mixtures of said compounds.

In a particular embodiment, the amount of di- or tri-valent cation added to the mixture is such to obtain a weight ratio soybean protein/metal cation ranging from 1:1 to 100:1, preferably from 2:1 to 80:1, even more preferably from 5:1 to 60:1, most preferably from 10:1 to 40:1.

More preferably, the soybean protein and the metal cation are added in the process of the invention in a weight ratio ranging from 1:1 to 100:1. This weight ratio allows obtaining a uniform dispersion of microparticles in the medium where they are form, without the formation of precipitates or aggregates. Furthermore, it confers microparticles with a regular morphology, namely a uniform and spherical shape, in contrast to a fusiform morphology obtained when higher ratios are used (see comparative example 1).

More preferably, the soybean protein and the metal cation are added in the process of the invention in a weight ratio ranging from 2:1 to 80:1, even more preferably from 5:1 to 60:1, most preferably from 10:1 to 40:1.

Actually, after mixing the soybean protein, the probiotic bacteria and the di- or tri-valent metal cation under the aforementioned conditions, i.e., at room temperature and under stirring, the microparticles of the invention are spontaneously formed. In a particular embodiment, said microparticles are in suspension in the medium in which they have been obtained.

Thus, contrary to other processes described in the prior art, such as the process described in WO2008/076975 where a gel is previously formed after mixing the different components and additional steps of lyophilization, grounding and sieving are required to obtain microsized structures, the process of the invention allows the formation of a uniform dispersion of microparticles by means of simple coacervation, leading to solid microspheres having a matrix-type structure wherein the probiotic bacteria is distributed, more preferably homogeneously distributed, within the whole matrix structure.

Therefore, the microparticles obtained by the process of the invention can be considered as self-assembling microparticles which are spontaneously formed by means of local interactions upon mixture of the bacteria suspension with the soybean protein dispersion in the presence of the metal cation. On the contrary, the microstructures described in WO2008/076975 correspond to irregular crystals or little pieces of gel obtained as a consequence of the additional steps, such as lyophilization, grounding and sieving, to which the gel previously formed is subjected, thus leading to microsized systems having different rearrangement.

Thus, the present invention also refers to self-assembling microparticles obtainable by the process of the present invention. More particularly, the invention refers to a self-assembling microparticles suspension obtainable by the process as defined above.

In a preferred embodiment, the suspension resulting from the mixing of soybean protein, probitic bacteria and di- or tri-valent metal cation which contains the microparticles of the invention is subjected to a drying treatment by conventional methods, for example vacuum drying or, advantageously by means of spray drying or by means of lyophilization, in order to dry the microparticles of the invention. This drying treatment allows obtaining the microparticles of the invention in the form of powder, which contributes to increase the stability thereof.

In a particular embodiment, this drying treatment, particularly when it is performed by means of spray drying or by means of lyophilization, comprises adding a protecting agent to the microparticles of the invention once they are formed. This protecting agent protects the matrix and the probiotic bacteria during the drying process thereof, such as for example, a saccharide or generally a suitable food additive, which in addition to the protective role, acts as a prebiotic. Non-limiting, illustrative examples of saccharides which can be used as protecting agents within the context of the present invention include lactose, mannitol, sucrose, maltodextrin, glucose, sorbitol, etc., as well as polysaccharides with prebiotic characteristics, such as for example, oligofructose, pectin, inulin, oligosaccharides (e.g. galactooligosaccharides, human milk oligosaccharides), lactulose, dietary fiber, etc. and mixtures thereof. In a particular embodiment, the protecting agent is selected from maltodextrin, inulin, fructooligosaccharides (FOS) and combinations thereof. If the microparticles of the invention include a protecting agent, this is added in the suitable amount; even though the by weight ratio of the matrix of microparticles and the protecting agent can vary within a wide range, in a particular embodiment, the matrix soybean protein:protecting agent by weight ratio is 1:0.1-5, typically 1:0.5-4, preferably about 1:1.

In a particular embodiment in which the method of the invention comprises drying the suspension of microparticles of the invention, said suspension of microparticles of the invention are dried by means of spray drying. To that end, the suspension containing the microparticles of the invention and the protecting agent is introduced in a spray-dryer and the processing conditions [air inlet temperature, air outlet temperature, air pressure, sample pumping rate, suction, and airflow] are controlled. The person skilled in the art can set the processing conditions that are most suitable for each case.

The method of the invention allows obtaining the microparticles of the invention in the form of a dry powder, which contributes to the stability of the microparticles of the invention during long storage periods under controlled or environmental conditions and it can also be easily incorporated in different intended solid and liquid products (e.g., foods, etc.).

Since the microparticles are formed previously to the addition of the protecting agent, this does not form any conjugate or complex with the soybean protein.

The microparticles obtainable after conducting said drying process thus constitute an additional aspect of the present invention. Accordingly, the invention also refers to self-assembling microparticles obtainable by the process of the invention which includes the drying treatment mentioned above.

More particularly, the invention refers to a dry powder of self-assembling microparticles obtainable by the process of the invention which includes the drying treatment mentioned above.

Applications

The microparticles of the invention have the capacity to encapsulate or entrap probiotic bacteria and to protect them during processing and from the "acidic-peptic" conditions during transit through the gastrointestinal tract once administered. The inactivation of the probiotic bacteria after incorporation in the different intended products (e.g., foods, etc.) is thus prevented or substantially reduced.

Therefore, in another aspect, the invention relates to a composition, hereinafter "composition of the invention" comprising at least one self-assembling microparticle as defined above, or at least one self-assembling microparticle obtainable by means of the method of the invention, either in the form of a suspension or in dry powder form.

In a particular embodiment, said composition is selected from:
(a) a composition consisting in a plurality of self-assembling microparticles of the invention, or in a plurality of self-assembling microparticles obtainable by means of the method of the invention, or in a plurality of self-assembling microparticles of the invention and of self-assembling microparticles obtainable by means of the method of the invention; and
(b) a composition comprising at least one self-assembling microparticle of the invention, and/or a self-assembling microparticle obtainable by means of the method of the invention, and a food, nutraceutical, cosmeceutical or pharmaceutical acceptable vehicle.

The characteristics of the self-assembling microparticles of the invention have already been defined above and are incorporated herein by reference.

In a particular embodiment, the self-assembling microparticles of the invention are in the form of a dry powder in the composition of the invention.

In the first case, the composition of the invention (a) is made up only and exclusively of self-assembling microparticles of the invention and/or of self-assembling microparticles obtainable by means of the method of the invention.

In the second case, the composition of the invention (b) comprises at least one self-assembling microparticle of the invention and/or a self-assembling microparticle obtainable by means of the method of the invention, and a food, nutraceutical, cosmeceutical or pharmaceutical acceptable vehicle or carrier.

The person skilled in the art will understand that the microparticles of the invention or the compositions containing them can be part of a food or feed, or of a nutraceutical, pharmaceutical, or cosmeceutical product, which constitutes an additional aspect of the present invention.

Thus, a further aspect of the present invention relates to a food, pharmaceutical, cosmeceutical or nutraceutical product comprising i) at least one self-assembling microparticle of the invention and/or a self-assembling microparticle obtained by means of the method of the invention, or ii) a composition comprising at least one self-assembling microparticle of the invention and/or one self-assembling microparticle obtainable by means of the method of the invention, whatever composition (a) or composition (b). Said product can be in a liquid, semi-solid or solid form.

In a particular embodiment, the product of the invention is a food or feed comprising i) at least one self-assembling microparticle of the invention and/or one self-assembling microparticle obtainable by means of the method of the invention, or ii) a composition comprising at least one self-assembling microparticle of the invention and/or one self-assembling microparticle obtainable by means of the method of the invention, and a food acceptable vehicle or carrier.

As used herein, the term "food" is any substance or product of any nature, solid or liquid, natural or processed which due to its characteristics, applications, components, preparation and state of preservation, can usually or ideally be used for some of the following purposes: a) as normal nutrition for human beings or animals or as pleasurable foods; or b) as dietetic products, in special cases of human or animal food. The term "feed" includes all the natural materials and finished products of any origin which, separately or conveniently mixed with one another, are suitable as animal food. Examples include cattle feed, chicken feed, horse feed, poultry feed.

A ready-to-eat food is that which does not need to be diluted by means of an aqueous solution suitable for consumption for example. In principle, the ingredients present in a ready-to-eat food are balanced and there is no need to add additional ingredients to the food to make it ready to eat, such considered by a person skilled in the art. A concentrated food is that in which one or more ingredients are present at a higher concentration than in a ready-to-eat food, therefore for use it is necessary to dilute it by means of an aqueous solution suitable for consumption for example. Non-limiting, illustrative examples of foods provided by this invention include both dairy products and derivatives, for example, fermented milks, yoghurt, kephir, curd, cheeses, butters, ice creams, milk-based desserts, etc., and non-dairy products, such as baked products, cakes and pastries, cereals, chocolates, jams, juices, other fruit derivatives, oils and margarines, prepared dishes, etc.

In another particular embodiment, the product of the invention is a nutraceutical product comprising i) at least one self-assembling microparticle of the invention and/or one self-assembling microparticle obtainable by means of the method of the invention, or ii) a composition comprising at least one self-assembling microparticle of the invention and/or one self-assembling microparticle obtainable by means of the method of the invention, and a nutraceutical acceptable carrier. As used herein, the term "nutraceutical product" refers to a product suitable for use in human beings or animals, comprising one or more natural products with therapeutic action which provide a health benefit or have been associated with disease prevention or reduction, for example, probiotic bacteria, etc., and it includes dietary supplements presented in a non-food matrix (e.g., capsules, powder, etc.) of a concentrated natural bioactive product usually present (or not) in the foods and which, when taken in a dose higher than that existing in those foods, exerts a favorable effect on health which is greater than effect which the normal food may have. Therefore, the term "nutraceutical product" includes isolated or purified food products as well as additives or food supplements which are generally presented in dosage forms normally used orally, for example, capsules, tablets, sachets, drinkable phials, etc.; such products provide a physiological benefit or protection against diseases, generally against chronic diseases. If desired, the nutraceutical product provided by the invention can contain, in addition to the probiotic bacteria, one or more nutraceuticals (products or substances associated with disease prevention or reduction), for example, flavonoids, omega-3 fatty acids, etc., and/or one or more prebiotics (non-digestible food ingredients which stimulate probiotic activity and/or growth), for example, oligofructose, pectin, inulin, galacto-oligosaccharides, lactulose, human milk oligosaccharides, dietary fiber, etc.

In another particular embodiment, the product of the invention is a pharmaceutical product comprising i) at least one self-assembling microparticle of the invention and/or one self-assembling microparticle obtainable by means of the method of the invention, or ii) a composition comprising at least one self-assembling microparticle of the invention and/or one self-assembling microparticle obtainable by means of the method of the invention, and a vehicle or carrier suitable for oral, topical, rectal or vaginal administration; to that end, said product comprises a pharmaceutically acceptable vehicle or carrier comprising one or more excipients suitable for oral administration, for example, in the form of capsule, powder, granulate, tablet (coated or non-coated), sachet, matrix, suspension, etc., or a pharmaceutically acceptable vehicle or carrier comprising one or more excipients suitable for topical administration, for example, in the form of cream, ointment, salve, etc., or a pharmaceutically acceptable vehicle or carrier comprising one or more excipients suitable for rectal administration, for example, in the form of suppository, etc., or a pharmaceutically acceptable vehicle or carrier comprising one or more excipients suitable for vaginal administration, for example, in the form of bolus, suppository, etc.

In another particular embodiment, the product of the invention is a cosmeceutical product comprising i) at least one self-assembling microparticle of the invention and/or one self-assembling microparticle obtainable by means of the method of the invention, or ii) a composition comprising at least one self-assembling microparticle of the invention and/or one self-assembling microparticle obtainable by means of the method of the invention, and a cosmeceutical acceptable vehicle or carrier. As used herein, the term "cosmeceutical product" refers to a product suitable for use in the body or animal body comprising one or more cosmeceutical products (functional cosmetics, dermaceuticals or active cosmetics), i.e., topical hybrid products with cosmetic-pharmaceutical characteristics containing active ingredients having effect on user's skin, hair and/or nails, at higher and more effective concentrations, therefore they are located in an intermediate level between cosmetic and drug. Illustrative examples of cosmeceutical products include essential oils, ceramides, enzymes, minerals, peptides, vitamins, etc. The following examples illustrate the invention and must not be considered as limiting the same.

EXAMPLES

The following examples describe the method for the production of self-assembling microparticles comprising a solid matrix and probiotic bacteria, wherein the solid matrix comprises soybean protein and a divalent metal cation, and wherein the probiotic bacteria are distributed throughout the solid matrix. Unless otherwise indicated, the general methods used are described below for carrying out these examples.

General Methods

I. Soybean Flour Characterization

Figure 2A:
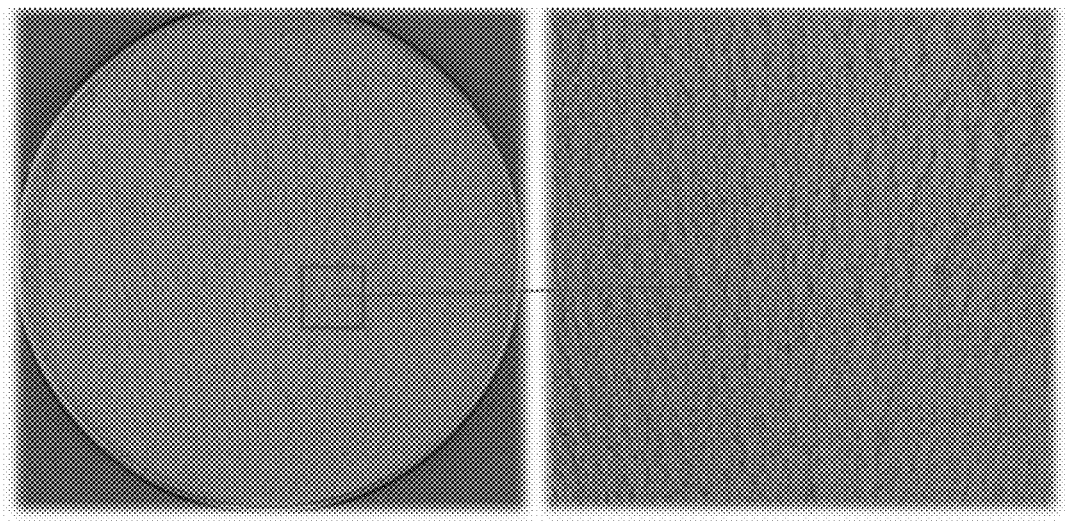
FIG. 2 shows photographs of the soybean flour from the soybean milk manufacturing before the extraction protein processing (a), and photographs of the soybean protein concentrate after drying and milling (b).

The soybean flour [FIG. 2a] was kindly provided from food industry where the soybean flour is generated as a residue during the soybean milk processing. The soybean flour was characterized in relation to its nutritive value in order to determine the homogeneity of different batches from the soybean milk production, especially with respect to the total protein content. For this purpose, the following parameters were determined: humidity, protein, fat, total dietary fiber, ash, carbohydrate, energy value, sugar profile, fatty acid profile, and sodium content. The humidity was determined by gravimetric analysis in an oven heated at 105±3° C. for 24 h up to constant weight. Protein content is obtained by Kjedhal method according to the protocol described in *Análisis de alimentos: métodos oficiales y recomendados por el Centro de Investigación y Control de la Calidad* (Ed. Ministerio de Sanidad y Consumo. Servicio de Publicaciones, 1985, p. 469). The total lipid content was determined following the method described by Bligh and Dyer (1959) and the fatty acid profile was determined by GC-FID (Gas Chromatography-Flame Ionization Detector) according the Regulation (EU) N° 1348/2013 of 16 Dec. 2013, where the preparation of fatty acid methyl esters (FAME) and GC analysis of FAME are described. The total dietary fibre was analyzed according the method described by AOAC International (991.43; J. AOAC Int. 75, 395, 1992). Ash content was determined by gravimetric analysis after the incineration of samples at 550±50° C. for at least 8 hours. Sugar profile was analyzed by HPLC-RI (High Performance Liquid Chromatography-Refractive Index). Carbohydrate content was calculated by difference. Energy value was calculated according to FAO recommendations.

The following table shows the results of the characterization of three different soybean flour batches produced as by-products from soybean milk processing.

TABLE 1

Nutritive value correspond to three different soybean flour batches

| PHYSICAL-CHEMICAL PARAMETERS | A | B | C |
| --- | --- | --- | --- |
| Nutritive Value (Group II) | | | |
| Humidity (g/100 g) | 11.9 | 10.7 | 11.4 |
| Proteins (g/100 g) | 35.28 | 32.41 | 32.67 |
| Fats (g/100 g) | 13.90 | 15.04 | 16.02 |
| Total dietary fibre (g/100 g) | 19.94 | 21.55 | 30.79 |
| Ashes (g/100 g) | 4.92 | 4.56 | 4.35 |
| Carbohydrates (g/100 g) | 14.06 | 15.74 | 4.77 |
| Energy value (kJ/100 g) | 512.60 | 547.43 | 475.54 |
| Sugar profile | | | |
| Fructose (g/100 g) | 1.72 | 1.34 | 1.19 |
| Glucose (g/100 g) | 1.45 | 1.37 | 0.76 |
| Sucrose (g/100 g) | 2.40 | 3.17 | 3.03 |
| Maltose (g/100 g) | <0.50 | <1.00 | <0.50 |
| Lactose (g/100 g) | <0.50 | <1.00 | <0.50 |
| Fatty acids profile | | | |
| Caproic acid (g/100 g fat) | <0.03 | <0.03 | <0.03 |
| Caprylic acid (g/100 g fat) | <0.02 | <0.02 | <0.02 |
| Capric acid (g/100 g fat) | <0.02 | <0.02 | <0.02 |
| Lauric acid (g/100 g fat) | <0.02 | 0.04 | <0.02 |
| Myristic acid (g/100 g fat) | 0.12 | 0.13 | 0.11 |
| Myristoleic acid (g/100 g fat) | <0.02 | <0.02 | <0.02 |
| Palmitic acid (g/100 g fat) | 11.89 | 12.60 | 13.69 |
| Palmitoleic acid (g/100 g fat) | 0.08 | 0.09 | 0.07 |
| Heptadecanoic acid (g/100 g fat) | 0.14 | 0.11 | 0.10 |
| Cis-10-heptadecanoic acid (g/100 g fat) | 0.04 | 0.04 | 0.04 |
| Elaidic acid (g/100 g fat) | <0.02 | <0.02 | <0.02 |
| Stearic acid (g/100 g fat) | 5.16 | 4.50 | 5.72 |
| Oleic acid (g/100 g fat) | 18.28 | 15.94 | 15.12 |
| Linolelaidic acid (g/100 g fat) | <0.02 | <0.02 | <0.02 |
| Linoleic acid (g/100 g fat) | 53.31 | 52.61 | 52.25 |
| Linolenic acid (g/100 g fat) | 9.14 | 13.11 | 11.77 |
| Arachidic acid (g/100 g fat) | 0.39 | 0.22 | 0.26 |

TABLE 1-continued

Nutritive value correspond to three different soybean flour batches

| PHYSICAL-CHEMICAL PARAMETERS | A | B | C |
|---|---|---|---|
| Cis-11-eicosanoic acid (g/100 g fat) | 0.20 | 0.16 | 0.13 |
| Arachidonic acid (g/100 g fat) | 0.03 | <0.02 | <0.02 |
| Cis-11-eicosapentanoic acid (g/100 g fat) | 0.16 | <0.02 | <0.02 |
| Behenic acid (g/100 g fat) | 0.55 | 0.24 | 0.16 |
| Erucic acid (g/100 g fat) | 0.33 | 0.12 | 0.42 |
| Lignoceric acid (g/100 g fat) | 0.18 | <0.04 | <0.04 |
| Docosahexanoic acid (g/100 gfat) | <0.04 | <0.02 | <0.02 |
| Nervonic acid (g/100 g fat) | <0.02 | 0.09 | 0.14 |
| Total saturated fats (g/100 g fat) | 18.25 | 17.84 | 20.06 |
| Total monounsaturated fats (g/100 g fat) | 18.94 | 16.44 | 15.93 |
| Total poyunsaturated fats (g/100 g fat) | 62.81 | 65.72 | 64.02 |
| Total trans fats (g/100 g fat) | <0.02 | <0.02 | <0.02 |
| Sodium (mg/kg) | 61.8 | 24.4 | <20 |

The physical-chemical parameters barely changed between batches. The small differences observed did not influence the amino acid profile of the extracted proteins as discussed in Section III.

II. General Method for Extracting Soybean Protein from Soybean Flour

Figure 2B:
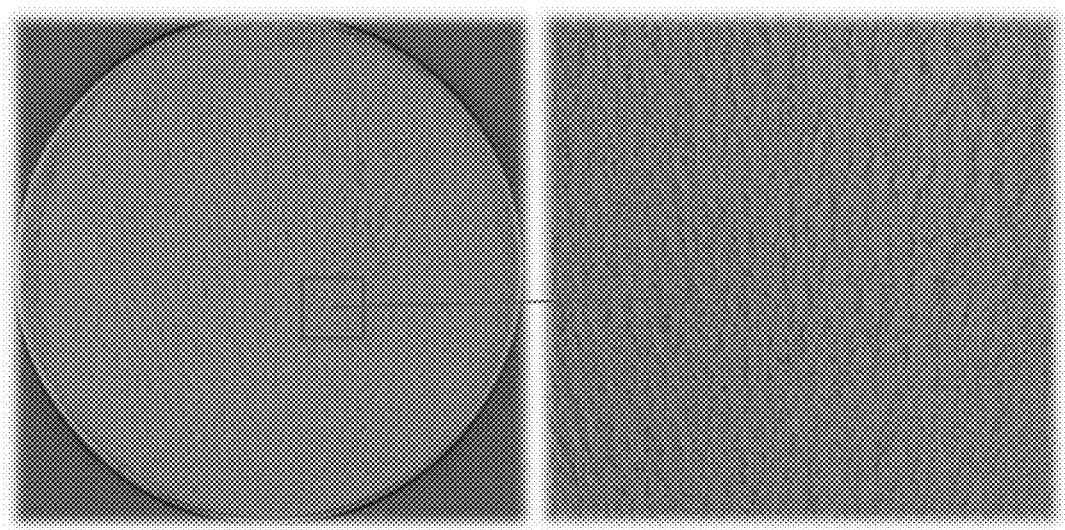

Firstly, the soybean flour was defatted with hexane (mixture of isomers) (by weight ratio soybean flour/hexane 1/10 p/p). Once the solvent was removed by centrifugation (10 min, 10,000 rpm) and by evaporation at room temperature, the soybean flour was moistened with water and sterilized in a rotary autoclave (Ferlo, model RF42J1P, San Adrián, España) at 121° C. for 15 minutes, according the treatment showed in FIG. 1. This heat treatment was necessary to eliminate the endogenous moulds, yeasts and bacteria from the soybean flour. Secondly, the protein was extracted using a pH 10 carbonate buffer solution (by weight ratio soybean flour/buffer 1/10 p/p) at 80° C. for 30 minutes (the extraction conditions were selected by design of experiments). The mixture was centrifuged at 10,000 rpm for 15 minutes. Finally, the protein was recovery from supernatant by isoelectric precipitation (pH 4.5) with a 10% HCl solution (v/v), filtered, dried by lyophilization and homogenized using a milling cutter. The resulting powder was cream coloured and fine (FIG. 2b).

III. Soybean Protein Characterization

Once the soybean protein was obtained, total protein content was determined by Kjeldhal method: 74.77±4.06 g/100 g (n=3, from different soybean flour batches produced throughout one year approximately).

Taking into account literature data, a soybean protein isolate (SPI) is characterized for having a protein concentration between 90% and 95%, whereas a soybean protein concentrate (SPC) is considered when the protein content is between 65% and 70%.

The soybean protein used in the examples herein provided for producing microparticles containing probiotic bacteria had a total protein concentration between a SPC and a SPI.

Additionally, the amino acid profile (except tryptophan) was carried out by acid hydrolysis according to the method ISO 13903:2005, using HPLC with ion exchange column, device for ninhydrin, post column derivatisation and photometric detector (Commission Regulation (EC) N° 152/2009 of 27 Jan. 2009 laying down the methods of sampling and analysis for the official control of feed). Particularly, cysteine and methionine were analyzed following the same method but from hydrolysates of oxidized samples.

For the determination of the total tryptophan, the soybean protein was hydrolysed under alkaline conditions with saturated barium hydroxide solution and heated to 100° C. for 20 hours. After hydrolysis internal standard (α-methyl-tryptophan) was added. The trypthophan and the internal standard were determined by HPLC with fluorescence detection (method EN ISO 13904).

The following table shows the amino acid profile of the soybean protein:

TABLE 2

Amino acid profile correspond to three different soybean flour batches

| AMINO ACID | Aa/TOTAL PROTEIN CONTENT (%) | | |
|---|---|---|---|
| | A | B | C |
| Aspartic Acid (Asp) | 11.71 | 11.59 | 11.58 |
| Serine (Ser) | 5.26 | 5.29 | 5.19 |
| Lysine (Lys) | 6.43 | 6.47 | 6.54 |
| Valine (Val) | 4.88 | 4.94 | 4.69 |
| Proline (Pro) | 5.45 | 5.48 | 5.46 |
| Alanine (Ala) | 4.20 | 4.38 | 4.34 |
| Threonine (Thr) | 3.85 | 3.95 | 4.03 |
| Phenylalanine (Phe) | 5.17 | 5.14 | 5.22 |
| Isoleucine (Ile) | 4.71 | 4.73 | 4.81 |
| Glycine (Gly) | 4.20 | 4.29 | 4.30 |
| Tyrosine (Tyr) | 3.66 | 3.68 | 3.61 |
| Arginine (Arg) | 7.51 | 7.35 | 7.43 |
| Leucine (Leu) | 7.85 | 7.93 | 7.81 |
| Histidine (His) | 2.59 | 2.63 | 2.62 |
| Glutamic acid (Glu) | 18.41 | 17.94 | 18.11 |
| Methionine (Met) | 1.37 | 1.39 | 1.38 |
| Cystein + Cystine (Cys) | 1.46 | 1.51 | 1.54 |
| Tryptophan (Total) (Trp) | 1.29 | 1.32 | 1.36 |

Table 2 shows that no significant differences were observed in the three batches.

IV. General Method for Producing Empty Soybean Protein and Divalent Metal Microparticles The materials, equipments and reagents were sterilized by heat treatment at 121° C. for 15 min. in an autoclave and/or ultraviolet radiation (20-40 min) and/or, disinfection by washing with 70% (v/v) ethanol and/or using a solution of bleach and soapy water.

The method for the production of soybean protein and a divalent metal cation microparticle comprises dissolving soybean protein in a pH 10 carbonate buffer solution by agitation for 20 minutes. Resultant dispersion was centrifuged at 10,000 rpm for 10 min., pellet was removed and supernatant was collected. A divalent metal solution such as calcium solution was added over the soybean protein solution to form microparticles of protein-metal coacervate. Once the microparticles were formed, a solution of a protecting agent such as maltodextrin, inulin or fructooligosaccharides (FOS) was added. The dispersion was finally dryed by spray-drying.

Unless otherwise indicated, the spray-dryer used in these examples was the Büchi B-290 Mini Spray-Dryer coupled to B-295 Inert Loop accessory (Büchi Switzerland, Flawil, Switzerland).

The maltodextrin used in these examples was Glucidex® from Roquette Frères (Lestrem, France). In particular formulations, a commercial blend of inulin and FOS was used (Orafty® Synergy 1) purchased from Beneo GmbH (Mannheim, Germany) was used.

V. Microparticles Characterization

The size of the microparticles was determined by means of confocal microscopy using a Nikon ECLIPSE 55 microscope with Colorview Soft Imaging Systems Camera DS-L2 (Tokyo, Japan).

Morphology analysis was additionally performed with a Transmission Electron Microscopy (TEM) Darwin 208 Philips 6080-100 kV coupled to an AMT camera.

VI. General Method for Preparing the Suspensions of Probiotic Bacteria

The probiotic bacteria used for carrying out these examples were *Lactobacillus plantarum* CECT 220 and *Lactobacillus casei* CECT 475 isolated from corn silage and cheese, respectively. The freeze-dried products of both microorganisms were revitalized in a MRS broth (Merck, Barcelona) at 37° C. under anaerobic atmosphere (85% nitrogen, 10% hydrogen, 5% carbon dioxide) in anaerobic chamber (MACS 500 AIRLOCK, AES Chemunex, Spain). 500 µl aliquots of stock suspensions which were kept frozen at −85° C. until the time of use were prepared from these revitalized cultures.

Suspensions were prepared as follows: 100 µl of the aliquot of the corresponding microorganism were transferred to 10 ml MRS broth. After incubation for 12 hours/37° C. under anaerobic conditions, the microscopic count was performed in a Thoma chamber in order to calculate the volume of sample that must be transferred to a 50 ml flask containing the MRS broth to reach a count of $10^6$ CFU/ml (colony forming units per milliliter). After inoculating that volume, the flasks were incubated in the previously described conditions for 24 hours until reaching the early stationary growth phase. The bacterial population was tracked and counted by means of seeding the corresponding decimal dilutions (0.1% Buffer Peptone Water (BPW) broth (Merck, Barcelona)) in MRS agar (Merck, Barcelona) at each sampling time.

The final working suspensions were prepared by centrifugation of a volume of 2-5 L MRS broth suspension at 10,000 rpm for 10 minutes. MRS broth was removed and the pellet was washed twice and resuspended in a solution of 2% sucrose (w/v).

VII. General Method for Producing Soybean Protein and Divalent Metal Microparticles Containing Encapsulated Probiotic Bacteria The general method for producing soybean protein and calcium microparticles containing encapsulated probiotic bacteria comprises the following steps: dissolving soybean protein obtained from soybean flour according to the method described in Section II in a pH 10 carbonate buffer solution, adding a specific volume of working bacteria suspension under stirring and with constant flow followed by the addition of a specific volume of a divalent metal solution. Optionally, a specific volume of a protecting agent was then added once microparticles were obtained.

Finally the microparticles were spray-dried.

VIII. General Method for Quantifying Viable Bacteria Present in the Formulation, and Determining the Bacterial Death Cycle Throughout the Process In order to determine the viable bacteria in microparticles, 1 ml of a solution of 0.1% BPW broth (w/v) was added to a known weight microparticles (1-2 mg), weighted with accurate precision in an analytical balance (Sartorius, SAR ME 235S, Göttingen, Germany). Microparticles were resuspended using a vortex for a few seconds followed by agitation in an orbital shaker (Eppendorf AG, Mixmate, Hamburg, Germany) at 900 rpm for 1 hour. After the disruption of microparticles which was checked by optical microscopy, the corresponding decimal dilutions were performed in 0.1% BPW broth (w/v) and seeded in MRS plates. After incubation at 37° C. under anaerobic conditions (MACS 500 Airlock chamber, AEX Chemunex, Spain) for 24-48 hours, colony counts were performed.

Taking into account the amount of bacteria initially included in the formulation before spray-drying per each gram of formulation and the counts obtained at the end of the process, the bacterial death cycles were determined by means of the following equation:

Bacterial death cycles=log(initial CFU/g)−log(recovered CFU/g)

IX. Method for the Evaluation of Resistance of Encapsulated Probiotic Bacteria and their Suspensions in Simulated Gastrointestinal Medium The gastrointestinal resistance of *L. plantarum* and *L. casei* assays were carried out according to the method described by Vinderola et al. (*Food Research International*, 2003, 36, 895-904).

For the evaluation of gastrointestinal resistance of bacteria, 10 µl of the bacterial suspension in culture medium or 1-2 mg (weighted with accurate precision) of microparticles were added to PVC tubes with 990 µl of simulated gastric fluid at pH 2.5. As many tubes were used as treatment times planned to be evaluated and taking into account three replicates, specifically 18 tubes (6 times×3 replicates). Nine of them with simulated gastric fluid corresponding to the times: 0.1, 0.5 and 2 hours (resistance to simulated gastric fluid) and 2.1, 5 and 8 hours (containing for 2 hours simulated gastric fluid and during 0.1, 3 and 6 hours under simulated intestinal fluid).

The simulated gastric fluid was prepared according to pharmacopeia and had the following composition for 1 liter of solution:

2 g NaCl (Sigma, Barcelona, Spain)

3.2 g pepsin from porcine gastric mucosa (Sigma, Barcelona, Spain)

37% HCl (v/v) to adjust the pH at 2.5

Sodium chloride and pepsin were dissolved in almost 1 liter of type I water and the pH was adjusted to 2.5. The solution was made up to 1 litre volume of type I water and filtered by 0.22 µm sterilized filter.

The simulated intestinal fluid was also prepared according to pharmacopeia:

6.8 g $KH_2PO_4$ (Panreac, Madrid, Spain) dissolved in 750 ml of type I water 10 g of pancreatin from porcine pancreas (Sigma, Barcelona, Spain)

0.2 N NaOH/0.2 HCl solutions to adjust the pH at 6.8

The samples were kept at 37° C. in an orbital shaker at 150 rpm for the corresponding time. Then the samples were extracted each time for survivor evaluation.

After 2 hours under simulated gastric conditions, samples were centrifuged at 10,000 rpm for 10 minutes and the supernatant was removed. The pellet was washed twice with 1 ml 0.1% BPW (w/v) before adding 990 µl of simulated intestinal fluid. The samples were kept in contact with the simulated intestinal fluid for 0.1, 3 and 6 hours (2.1, 5 and 8 hours after from the start of the assay). After those times were lapsed, the samples were centrifuged; the supernatants were discarded and the pellets were treated according to the method for the microparticle disruption described in Section VIII. The viable bacteria count was performed using the method of counting in a MRS agar plate describe in the same section.

The fraction of surviving bacteria was calculated according to the following equation:

$$\text{Log survivor fraction} = \text{Log}\left(\frac{N_t}{N_0}\right)$$

where $N_t$ represents the total viable bacteria after each time of treatment, and $N_0$ represents the initial number of inoculated bacteria (Bao et al., Food Control, 2010, 21 (5): 695-701).

X. Method for the Evaluation of the Stability of Microencapsulated Lactic Bacteria Over Storage Time Under Controlled Storage Conditions Microparticles containg probiotic bacteria were stored in polypropylene containers under controlled conditions at 25° C. and 60% Relative Humidity (RH) in a climate chamber (Memmert GmbH, HPP108, Schpolywabach, Germany). The following control samples were also performed:

Freeze-dryed bacteria as the commercial format nowadays
Spray-dried bacteria without forming microparticles from a suspension in a 2% sucrose (w/v) solution
Bacterial suspension in broth medium
Bacterial suspension in a 2% sucrose (w/v) solution.

XI. Method for the Evaluation of the Stability of Microencapsulated Lactic Bacteria in Acidic Conditions An additional experiment of stability of microparticles with respect to commercial non-encapsulated form (generally lyophile or bacterial suspension) was performed in order to demostrated the protective effect of the microparticles.

For this purpose, one of the soybean protein with calcium microparticles in the presence of a protecting agent (Sp) was chosen as a result of the improvement observed after the experiments performed according to methods described in Section IX and X.

The microparticles, lyophile and suspension were resuspended directly en HCl pH 3 with an initial bacteria count in the medium of $1 \times 10^7$-$1 \times 10^8$ CFU/ml approximately and the suspensions were stored at 4° C.

The viable counts were carried out according to the method described in Section VI in the case of evaluating the lyophile and the suspension. For the analysis of microparticles, an adjustment to a pH of 11 with 1% NaOH (w/v) was necessary to disrupt the microparticles.

XII. Method for the Evaluation of the Stability of Microencapusalted Lactic Bacteria in Food The microparticles of soybean protein and calcium in the presence of a protecting agent, Sp, were selected for the evaluation of the stability of bacteria in two different food products as aforementioned.

In this assay, lyophile was chosen as control sample because, nowadays, it is the most usual form for the commercialization of probiotics.

Both the microparticles and the lyophile were resuspended in two commercial food products (fresh milk and fresh orange juice), weighting the enough quantity for having a final product with a probiotic concentration ($\geq 10^7$ CFU/g). The resultant foods were stored at 4° C. for a period corresponds to the shelf-life of each product.

For the quantitation of bacteria counts, the method followed was similar to that described for the survival of *L. plantarum* in simulated gastrointestinal conditions (Section IX) but instead of being the bacteria in simulated GI fluids, were suspended in food fresh milk or fresh orange juice.

EXAMPLES

Example 1. Preparation and Characterization of Soybean Protein and a Divalent Metal Microparticles Containing Encapsulated Probiotic Bacteria of the Genus *Lactobacillus Plantarum* (Sp)

750 mg of soybean protein extracted from the soybean flour were dissolved in 25 ml of carbonate buffer solution adjusted to pH 10. The dispersion was stirred for 20 minutes and then centrifuged at 10,000 rpm for 10 minutes.

Over the supernatant under stirring, 2 ml of working bacterial solution (washed bacteria twice and resuspended in a solution of 2% sucrose (w/v): $1.9 \times 10^{11}$ CFU/ml) were added.

After five minutes, 30 ml of 0.2% $CaCl_2$ (w/v) (weight ratio soybean protein/$Ca^{2+}$ cation 35:1) were added and the mixture was incubated for 20 minutes under stirring. 750 mg of mannitol or maltodextrin were added to the mixture and the suspension was then dried by spray-drying.

The parameters of this process were:
Air inlet temperature: 85° C.
Air outlet temperature: 67° C. (approximately)
Suction: 100%
Sample pumping rate: 3.5 ml/min
Air pressure: −60 mbar
Airflow: 600 L/h (40-50 mm)

Figure 3:
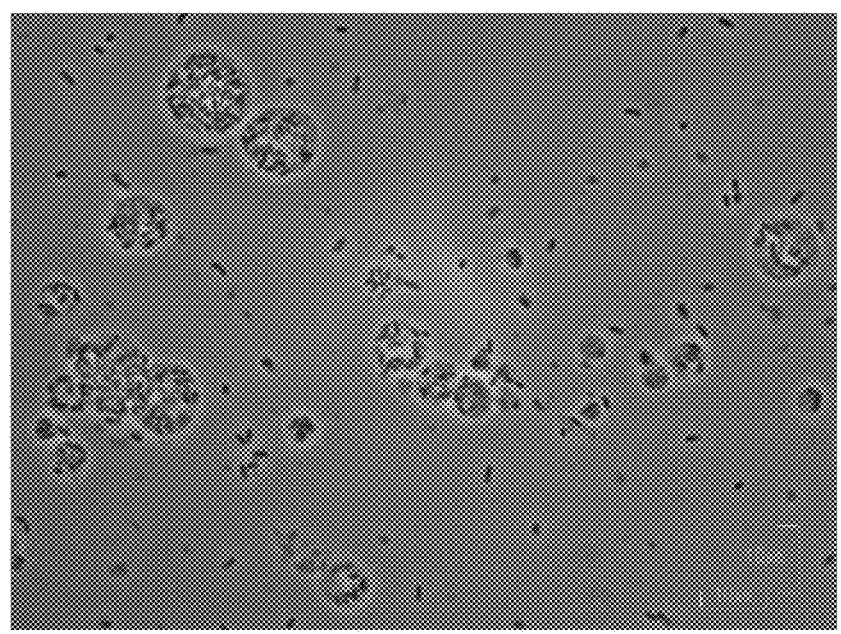
FIG. 3 shows a confocal microscopy image of soybean protein and calcium microparticles after spray-drying with encapsulated $L.$ $plantarum$ (×100). The scale in the lower right part represents 10 μm.
Figure 4:
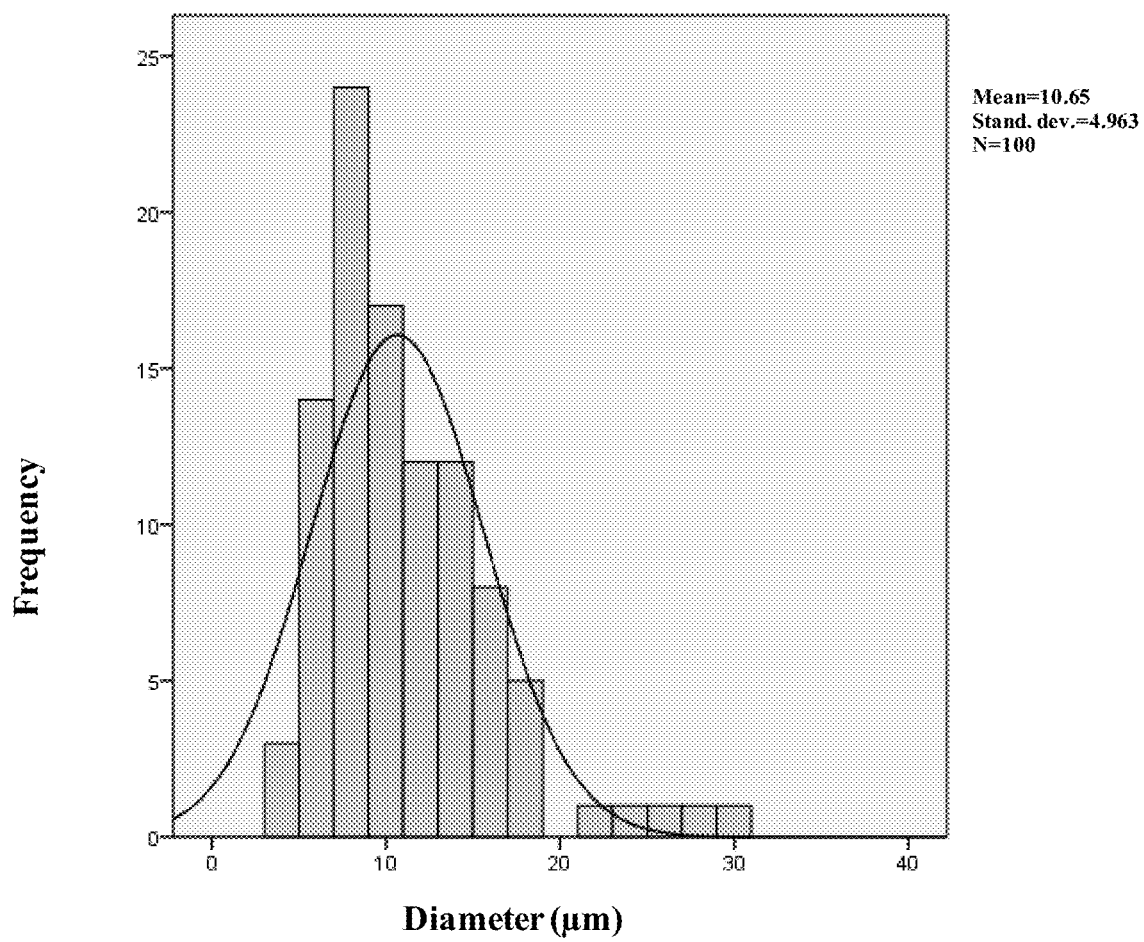
FIG. 4 is a histogram of the size distribution of the soybean and calcium microparticles containing $L.$ $plantarum$. Mean was calculated from the measure of the diameter of 100 microparticles using the software imaging system coupled the microscope.
Figure 5A:
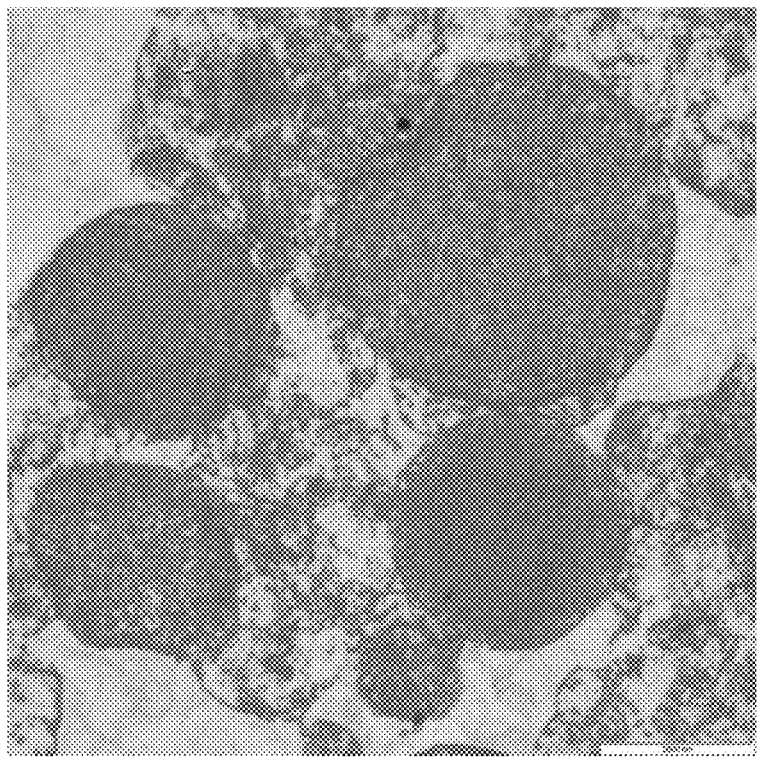
FIG. 5 shows the transmission electron microscopy images showing empty soybean protein and calcium microparticles (a, b, ×2520) and with encapsulated $L.$ $plantarum$ (c, ×2520; d, ×2000). The scale in the lower right part represents 2000 nm for images a), c) and d) and 1000 nm for image b). All images were captured using an energy filtering Zeiss LIBRA 120 transmission electron microscope (TEM) with a Gatan Ultrascan 1000 2k×2k CCD camera (accelerating voltage=80 kV).
Figure 5B:
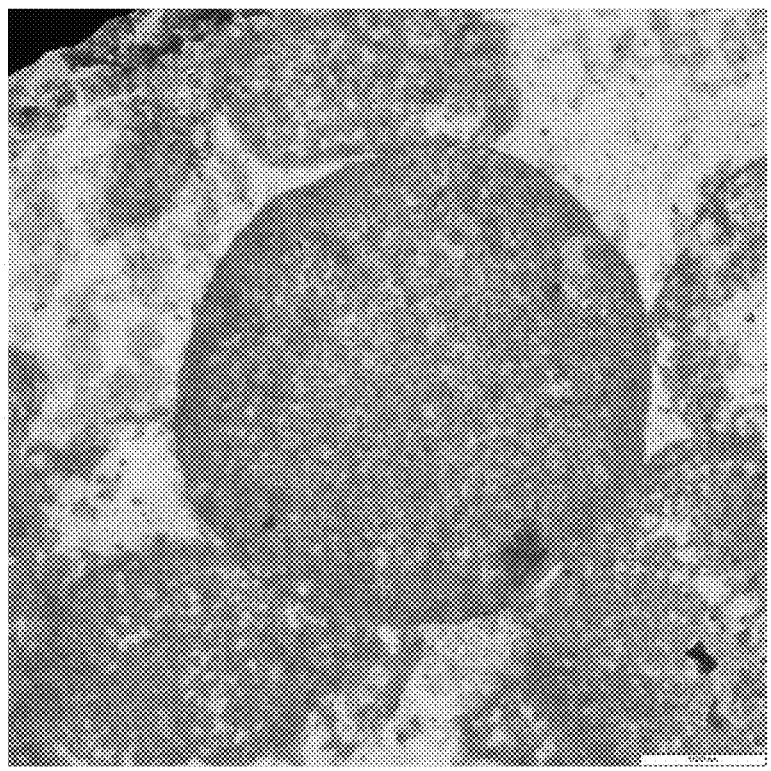
Figure 5C:
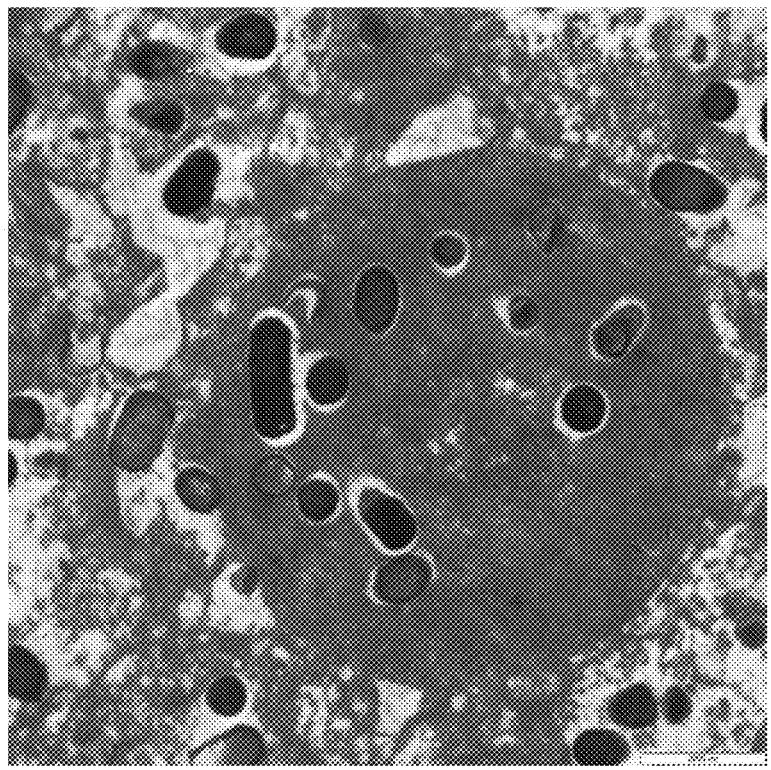
Figure 5D:
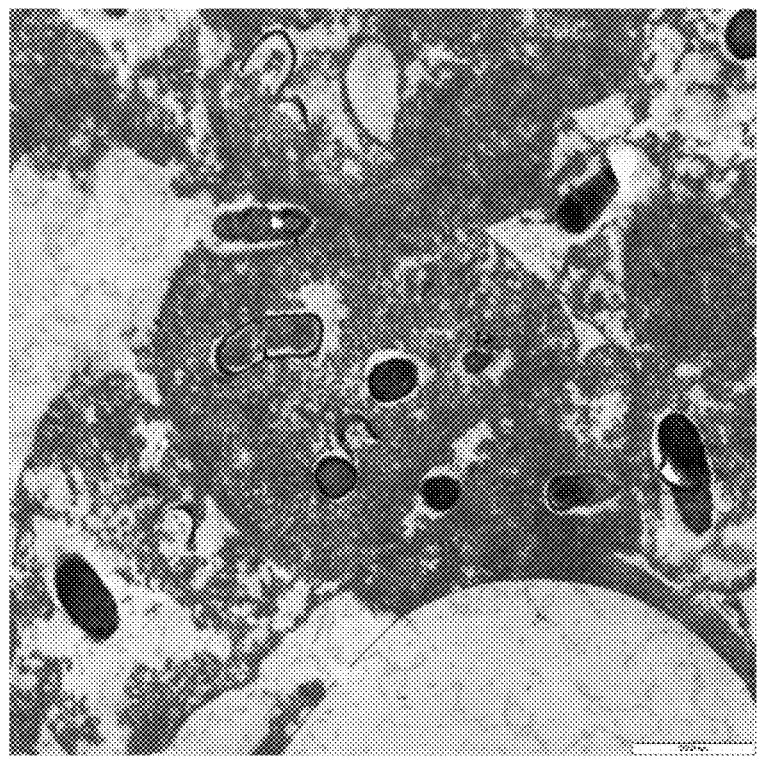

The microparticles collected in the form of cream colour powder, were characterized respect to their size and shape by confocal microscopy and transmission electron microscope (TEM). FIG. 3 shows the optical microscopy image obtained for the microparticles containing *L. plantarum* where the bacteria were entrapped within the soybean protein with calcium matrix. FIG. 4 is the histogram which represents the size distribution of the soybean particles with *L. plantarum* encapsulated, which was 11±5 µm. In FIG. 5 TEM images are observed both without bacteria (a, b) and containing *L. plantarum* (c, d), where probiotics are clearly seen in black, trapped and homogeneously distributed in the matrix of the microparticle. Therefore, this image demonstrate that the self-assembling microparticles provided by this invention, and/or the self-assembling microparticles obtainable by the process provided by this invention comprise a solid matrix and a probiotic bacteria, wherein the solid matrix comprises soybean protein and a divalent metal cation, and wherein the probiotic bacteria is distributed throughout the solid matrix.

In particular formulations, mannitol or maltodextrin was substituted by a commercial blend of inulin and FOS, partially or totally as follows:

TABLE 3

| Sp microparticle composition | | |
| --- | --- | --- |
| SAMPLE | MALTODEXTRIN (mg) | INULIN + FOS (mg) |
| Sp | 750 | — |
| Sp 250 | 500 | 250 |
| Sp 500 | 250 | 500 |
| Sp 750 | — | 750 |

Example 2. Evaluation of the Stability of Encapsulated *Lactobacillus Plantarum* Over Storage Under Controlled Conditions of Temperature and Relative Humidity (25° C./60% RH)

The formulations Sp, Sp 250, Sp 500 and Sp 750 described in Example 1 were used to evaluate the survival of the bacteria under controlled conditions of temperature and relative humidity. The microparticles were stored in 50 ml polypropylene containers in a climate chamber at 25° C. and 60% RH.

In order to compare the viability of *L. plantarum* in different formulations, the study was carried out for the following products: different microparticles of soybean protein and calcium in the presence of a protecting agent, non-encapsulated lyophilized *L. plantarum*, non-encapsulated spray-dried *L. plantarum*, fresh suspension of *L. plantarum* in MRS culture medium and fresh suspension of *L. plantarum* in 2% sucrose (w/v).

Figure 6:
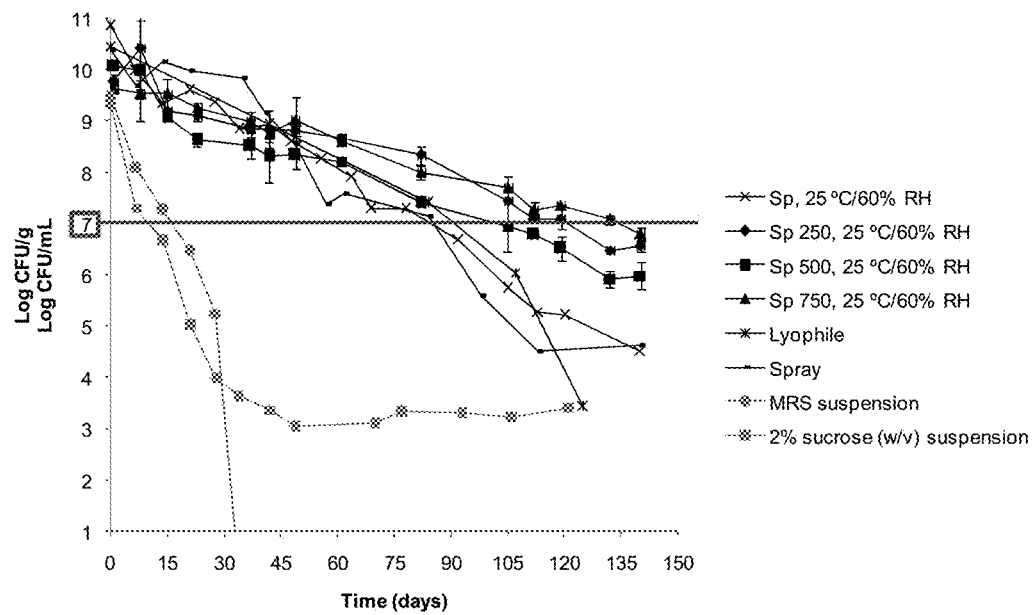
FIG. 6 is a graph showing the viability of $L.$ $plantarum$ under controlled conditions (25° C./60% RH) over time: $L.$ $plantarum$ encapsulated in soybean protein with calcium microparticles (Sp formulation); variations of this composition (Sp 250, Sp 500, Sp 750); non-encapsulated lyophilized $L.$ $plantarum$; non-encapsulated spray-dried $L.$ $plantarum$; fresh concentrated suspension of $L.$ $plantarum$ in MRS culture medium and fresh concentrated suspension of $L.$ $plantarum$ in 2% sucrose (w/v) solution.

The graph in FIG. 6 shows that in the first month of study was a loss of between 4 and 5 logarithmic units in the counts of both fresh suspensions. In the fourth month, losses of 7 logarithmic units were in the case of bacteria in lyophilized form having a probiotic concentration ($\geq 10^7$ CFU/g) for three months. In the case of non-encapsulated spray-dried *L. plantarum*, the probiotic concentration lasted three months, similar to the lyophile and Sp formulation. However, when *L. plantarum* is encapsulated in soybean protein and calcium microparticles in the presence of an adjuvant, mixture of maltodextrin, inulin and oligosacharides the probiotic concentration was remained between 2-6 weeks more, having the best results for Sp 750 formulation.

These results confirm that the encapsulation of *L. plantarum* in soybean protein and calcium microparticles in the presence of a protecting agent allowed enhance the viability of bacteria up to 6 weeks more with respect to the lyophile. Therefore, the probiotic concentration for the best formulation (Sp 750) lasted four and a half months.

Example 3. Evaluation of the Resistance of the Encapsulated Probiotic Bacteria of the Genus *Lactobacillus Plantarum* to Simulated Gastrointestinal Medium The formulations Sp, Sp 250, Sp 500 and Sp 750 described in Example 1 were selected to evaluate the resistance of the encapsulated bacteria in a simulated gastrointestinal medium following the method described in Section IX.

Figure 7:
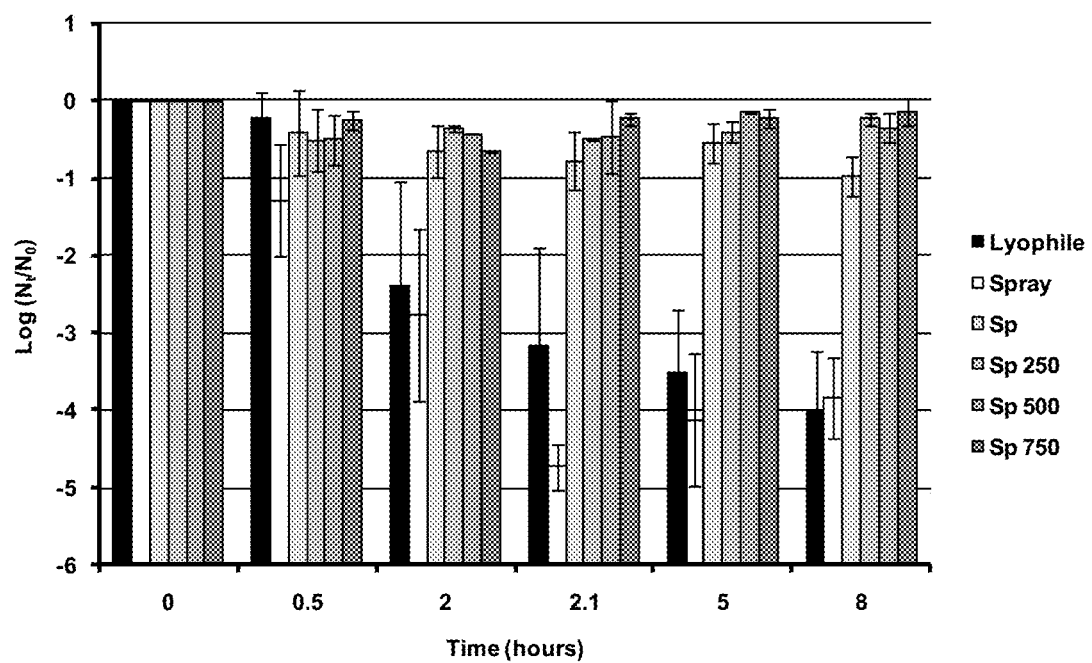
FIG. 7 is a graph showing the survival of $L.$ $plantarum$ in simulated gastrointestinal medium (0 to 2 hours: simulated gastric medium; 2.1 to 8 hours: simulated intestinal medium): non-encapsulated lyophilized $L.$ $plantarum$; non-encapsulated spray-dried $L.$ $plantarum$ and $L.$ $plantarum$ encapsulated in soybean protein and calcium microparticles (Sp, Sp 250, Sp 500, Sp 750).

FIG. 7 shows the results obtained for these microparticles in addition to the data for non-encapsulated lyophilized and spray-dried *L. plantarum*. In the case of non-encapsulated lyophilized and spray-dried *L. plantarum*, the number of viable counts decreased gradually throughout the study ending with a mean loss of 4 logarithmic units. In the case of microparticles, the counts for Sp 250, Sp 500 and Sp 750 were kept virtually constant throughout the entire assay, being significantly higher than the non-encapsulated *L. plantarum* formulations from the end of the assay in simulated gastric fluid (2 h) up to the end of the assay in simulated intestinal fluid (8 h). Although for the Sp formulation a reduction of a mean of one logarithmic unit was observed at the end of the entire assay, its number of viable counts was also significantly higher than the non-encapsulated *L. plantarum* forms from the end of the assay in simulated gastric fluid (2 h) up to the end of the assay in simulated intestinal fluid (8 h).

In conclusion, this study demonstrated that the microparticles selected significantly enhanced the tolerance of *L. plantarum* to simulated gastrointestinal fluids in a mean of 3-4 logarithmic cycles with respect to the non-encapsulated forms.

Example 4. Evaluation of the Survival of Encapsulated *Lactobacillus Plantarum* in Acidic Conditions (HCl pH 3)

The microparticles Sp formulated as described in Example 1, which improved the survival of *L. plantarum* under simulated gastrointestinal fluids, were selected to perform an additional experiment in acidic conditions.

Figure 8:
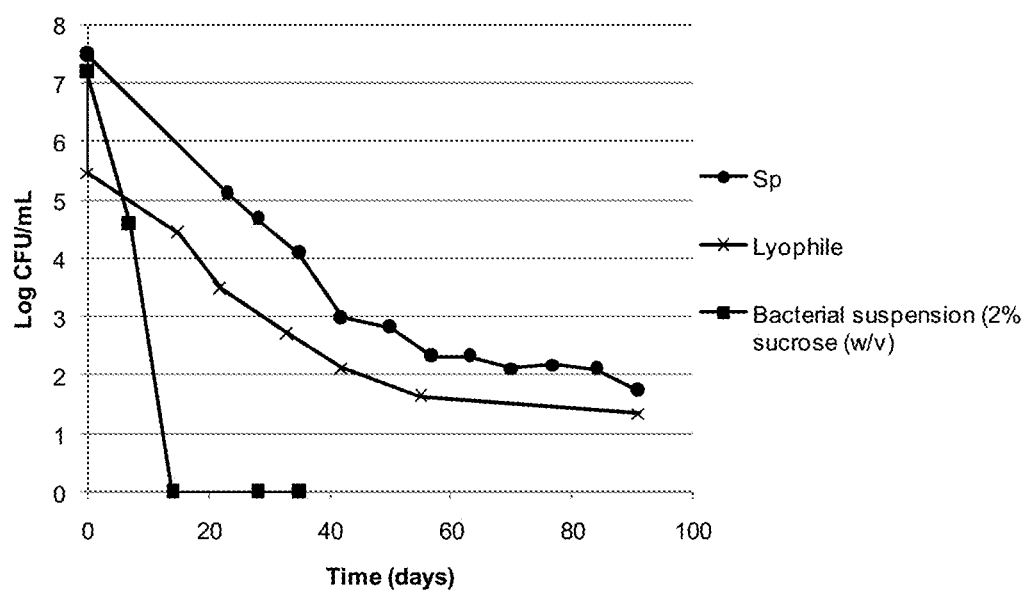
FIG. 8 shows the viability of $L.$ $plantarum$ in acidic conditions (HCl pH 3) for different forms: microparticles of soybean protein with calcium in the presence of a protecting agent (Sp), lyophile and suspension in 2% sucrose (w/v).

The assay was carried out according to the method described in Section XI. FIG. 8 shows an improvement of the survival of the probiotics for the encapsulated *L. plantarum*. The bacteria counts fell almost 3 logarithmic units in a week for the suspension form and decreased to <10 CFU/ml (detection limit) in two weeks.

It is remarkable that the viable counts for the lyophile were reduced dramatically (2 logarithmic units) at the beginning of the experiment whereas the same reduction was observed in the case of the microparticles but one month later. At the end of the experiments (approximately 3 months), both of formulations had similar bacteria counts.

Example 5. Evaluation of the Survival of Encapsulated *Lactobacillus Plantarum* in Food As additional evaluation of the survival of microorganisms, and in a similar way that described in Example 4, Sp microparticles were chosen for food formulation.

The microparticles and lyophile were added to fresh milk and fresh orange juice in a probiotic concentration. The viable bacteria were count throughout the shelf-life of each product according to the same protocol described in Section XI.

Figure 9A:
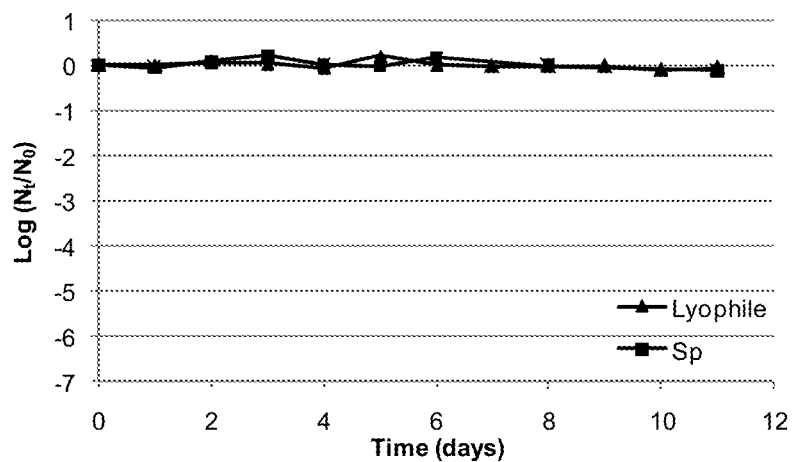
FIG. 9 shows the viability of $L.$ $plantarum$ in fresh milk (a) and fresh orange juice (b) for microparticles of soybean protein with calcium in the presence of a protecting agent (Sp) and lyophile.
Figure 9B:
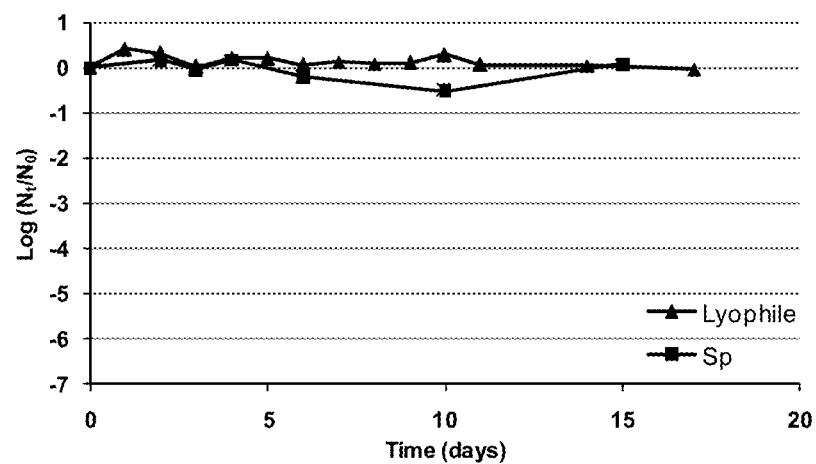

FIG. 9 shows that virtually were not differences between adding microparticles or lyophile for both food products.

Example 6. Preparation and Characterization of Soybean Protein and a Divalent Metal Microparticles Containing Encapsulated Probiotic Bacteria of the Genus *Lactobacillus Casei* (Sc)

750 mg of soybean protein extracted from the soybean flour were dissolved in 25 ml of carbonate buffer solution adjusted to pH 10. The dispersion was stirred for 20 minutes and then centrifuged at 10,000 rpm for 10 minutes.

Over the supernatant under stirring, 2 ml of working bacterial solution (washed bacteria twice and resuspended in a solution of 2% sucrose (w/v): $1.7 \times 10^{10}$ CFU/ml) were added.

After five minutes, 18 ml of 1% $CaCl_2$ (w/v) (weight ratio soybean protein/$Ca^{2+}$ cation 12:1) were added and the mixture was incubated for 20 minutes under stirring. 750 mg of mannitol or maltodextrin were added to the mixture and the suspension was then dried by spray-drying.

The parameters of this process were:
Air inlet temperature: 85° C.
Air outlet temperature: 67° C. (approximately)
Suction: 100%
Sample pumping rate: 3.5 ml/min
Air pressure: −60 mbar
Airflow: 600 L/h (40-50 mm)

The microparticles collected in the form of cream colour powder were analysed respecting their viable count which was of $1.5 \times 10^{10}$ CFU/g after the spray-drying.

Example 7. Evaluation of the Stability of Encapsulated *Lactobacillus Casei* Over Storage Under Controlled Conditions of Temperature and Relative Humidity (25° C./60% RH)

The formulation Sc described in Example 6 was used to evaluate the survival of the bacteria under controlled conditions of temperature and relative humidity. The microparticles were stored in 50 ml polypropylene containers in a climate chamber at 25° C. and 60% RH.

In a similar way to Example 2, in order to compare the viability of *L. casei* in different formulations, the study was carried out for the following products: microparticle of soybean protein and calcium in the presence of a protecting agent, non-encapsulated lyophilized *L. casei*, non-encapsulated spray-dried *L. casei*, fresh suspension of *L. casei* in MRS culture medium and fresh suspension of *L. casei* in 2% sucrose (w/v).

Figure 10:
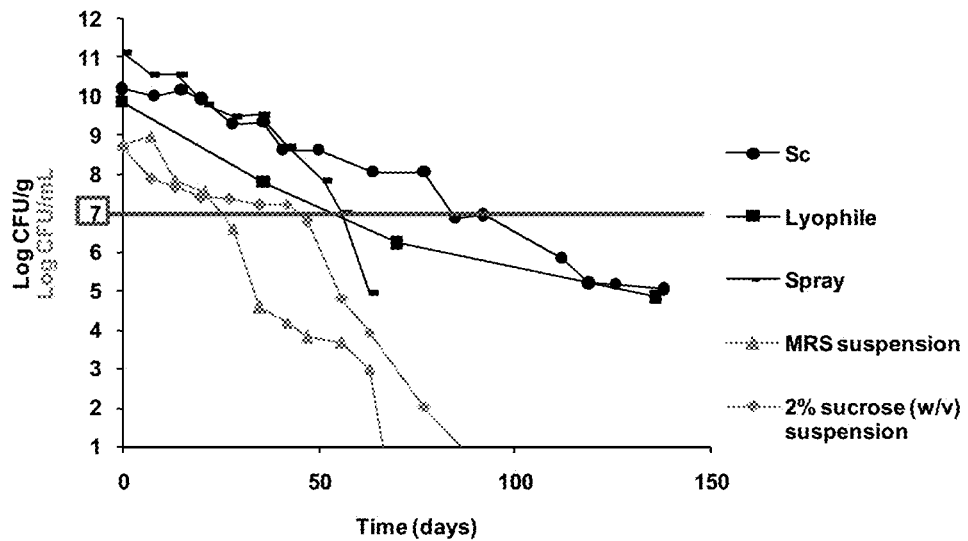
FIG. 10 is a graph showing the viability of $L.$ $casei$ under controlled conditions (25° C./60% RH) over time: $L.$ $casei$ encapsulated in soybean protein with calcium microparticles in the presence of a protecting agent (Sc formulation); non-encapsulated lyophilized $L.$ $casei$; non-encapsulated spray-dried $L.$ $casei$; fresh concentrated suspension of $L.$ $casei$ in MRS culture medium and fresh concentrated suspension of $L.$ $casei$ in 2% sucrose (w/v) solution.

The graph in FIG. 10 shows that in the first month of study was a loss of between 4 and 5 logarithmic units in the counts of fresh MRS suspension whereas for 2% sucrose (w/v) the decreased was only in one logarithmic unit. However, after two months, the viable counts were of $10^4$ CFU/ml. In the third month, losses of 3 logarithmic units were in the case of bacteria in lyophilized form and loss of 5 logarithmic units were reaching in the fifth month. In the case of non-encapsulated spray-dried *L. casei*, the probiotic concentration lasted two months, similar to the lyophile. However, when *L. casei* is encapsulated in soybean protein and calcium microparticles in the presence of a protecting agent (maltodextrin) the probiotic concentration was remained one month more.

These results confirm that the encapsulation of *L. casei* in soybean protein and calcium microparticles in the presence of a protecting agent allowed enhance the viability of bacteria up to 4 weeks more with respect to the lyophile.

Example 8. Evaluation of the Resistance of the Encapsulated Probiotic Bacteria of the Genus *Lactobacillus Casei* to Simulated Gastrointestinal Medium The formulation Sc described in Example 6 was selected to evaluate the resistance of the encapsulated bacteria in a simulated gastrointestinal medium following the method described in Section IX.

Figure 11:
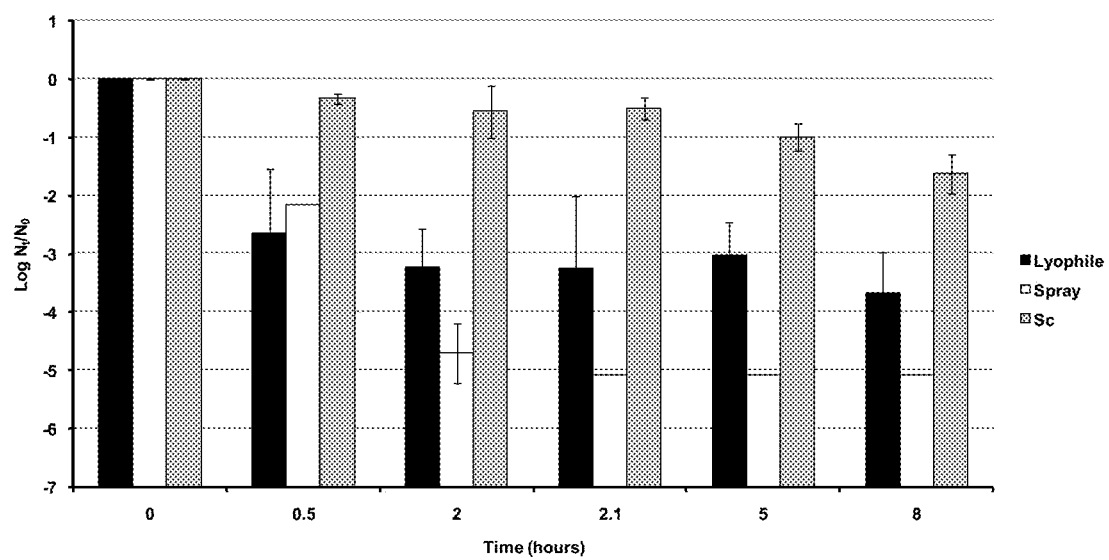
FIG. 11 is a graph showing the survival of $L.$ $casei$ in simulated gastrointestinal medium (0 to 2 hours: simulated gastric medium; 2.1 to 8 hours: simulated intestinal medium): non-encapsulated lyophilized $L.$ $casei$; non-encapsulated spray-dried $L.$ $casei$ and $L.$ $casei$ encapsulated in soybean protein and calcium microparticles in the presence of a protecting agent (Sc).

FIG. 11 shows the results obtained for these microparticles in addition to the data for non-encapsulated lyophilized and spray-dried *L. casei*. In the case of non-encapsulated lyophilized *L. casei*, the number of viable counts decreased throughout the study ending with a mean loss of 4 logarithmic units whereas the survival counts for the spray-dried form fell up to 5 logarithmic units. In the case of microparticles, the counts for Sc were kept virtually constant during the assay in simulated gastric fluid. At 2.1 h after the start of the experiment, a loss of one logarithmic unit was observed, ending the study with a mean loss of 1.6 logarithmic units. Therefore, the survival throughout the assay was significantly higher for the encapsulated *L. casei* than the non-encapsulated formulations.

In conclusion, this study demonstrated that the microparticles selected significantly enhanced the tolerance of *L. casei* to simulated gastrointestinal fluids with respect to the non-encapsulated forms.

Comparative Example 1. Evaluation of the Influence of the Ratio Soybean Protein/$Ca^{2+}$ in the Formation of Microparticles For comparative purposes, example 1 was reproduced but using a smaller amount of the divalent metal, so as weight ratio soybean protein/$Ca^{2+}$ was 122:1.

750 mg of soybean protein extracted from the soybean flour were dissolved in 25 ml of carbonate buffer solution adjusted to pH 10. The dispersion was stirred for 20 minutes and then centrifuged at 10,000 rpm for 10 minutes.

Over the supernatant under stirring, 2 ml of working bacterial solution (washed bacteria twice and resuspended in a solution of 2% sucrose (w/v): $3 \times 10^{10}$ CFU/ml) were added.

After five minutes, 8.5 ml of 0.2% $CaCl_2$ (w/v) (weight ratio soybean protein/$Ca^{2+}$ cation 122:1) were added and the mixture was incubated for 20 minutes under stirring.

A comparison between the suspension obtained according to example 1 and that obtained according to comparative example 1 showed that the weight ratio 35:1 (example 1) allowed the coavervation process to better proceed, obtaining a uniform dispersion of microparticles without formation of precipitates or aggregates.

750 mg of mannitol or maltodextrin were added to the mixture and the suspension was then dried by spray-drying. The parameters of this process were:
Air inlet temperature: 85° C.
Air outlet temperature: 67° C. (approximately)
Suction: 100%
Sample pumping rate: 3.5 ml/min
Air pressure: −60 mbar
Airflow: 600 L/h (40-50 mm)

The yield of this process was 16% lower than the observed in the Example 1.

The microparticles were characterized by confocal microscopy and comparing the morphology with respect to that microparticles obtained in the Example 1.

Figure 12:
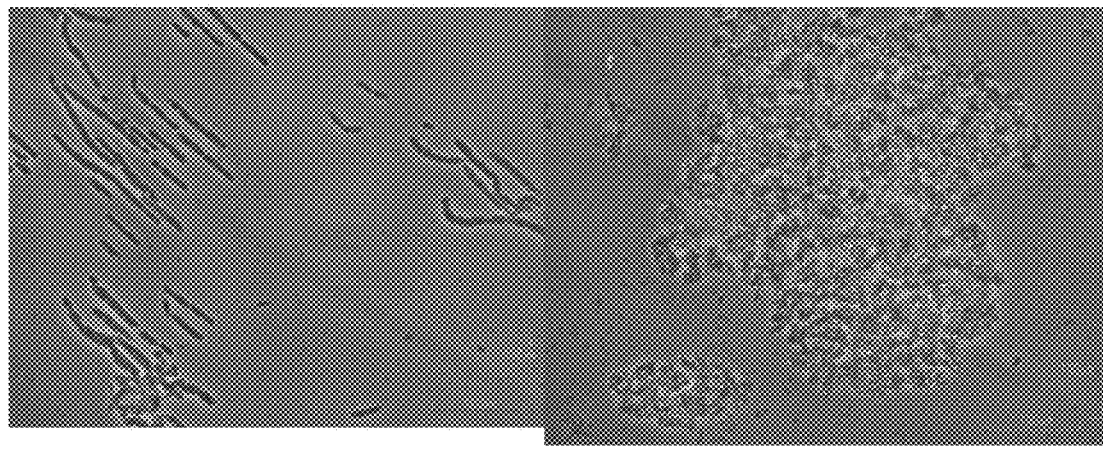
FIG. 12 shows optical microscopy images of particles obtained using a weight ratio (soybean protein)/$Ca^{2-}$ of: (a) 122:1 (w/w) (before drying); (b) 35:1 (w/w) (before drying); (c) 122:1 (w/w) (after drying); (d) 35:1 (w/w) (after drying).
Figure 12:
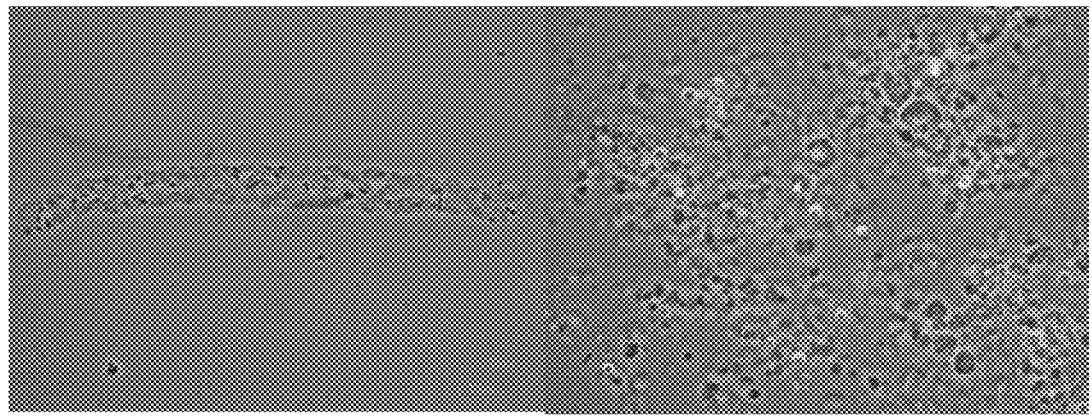

As shown in FIG. 12, a weight ratio of soybean protein/$Ca^{2+}$ of 35:1 conferred microparticles with a uniform spherical morphology, in contrast to a fusiform morphology obtained when a ratio 122:1 is used, both before and after the drying process.

According to the method described in section VIII, the microparticles were collected in the form of cream colour powder and they were analyzed respecting their viable count which was of $3.5 \times 10^{10}$ CFU/g after the spray-drying.

Comparative Example 2. Reproduction of the Process Described in WO2008/076975 Using a Soybean Protein/$Ca^{2+}$ Ratio According to the Present Invention Example 1 of the application WO2008/076975 was reproduced in a similar way but using a ratio soybean protein/$Ca^{2+}$ of 35:1 (w/w) according to the present invention.

A. Alginate as Constituent of the Hydrogel Composition 30 g of sacarose (Scharlau, Mas D'en Cisa, Spain) was added to 100 ml water and allowed to completely dissolve. Soy protein isolate (3 g, ProFam® 646, ADM, USA). was added under vigorous mixing using an Ultraturrax®. Sodium alginate (1 g, Sigma, Barcelona, Spain) was then mixed into the slurry and allowed to cool down to room temperature. *Lactobacillus plantarum* CECT 220 (10 g concentrated from fermentation harvest) was then added to the slurry under vigorous mixing until a smooth and uniform gel achieved.

The basic formulation was then extruded into a 100 ml bath (held at 0-5° C.) containing 0.24 g $CaCl_2$ and 30 g sacarose using a syringe equipped with 20 G needle. The $CaCl_2$ bath was gently stirred while injecting the slurry. The matrix strings or drops were allowed to cross-link for 30 minutes and then harvested and bottled on paper towel. The strings or drops were first dried in a convection oven at 35° C. until water activity was reduced to 0.6. Then, they were frozen at 80° C. and freeze-dried for about 24 hours. The dry strings or drops were then ground to fine powder using standard coffee grinder and sieved through 50-200 micron screens.

The viability of resultant microparticles was analyzed and the viable cell was lower than 2.5 CFU/g.

B. Chitosan as Constituent of the Gel Composition

The process followed in this section was similar to that described in Section A but replacing completely the alginate by the same amount of chitosan (Guinama, Valencia, Spain).

The viability of resultant microparticles was analysed and the viable cell was lower than 5.7 CFU/g.

Figure 13:
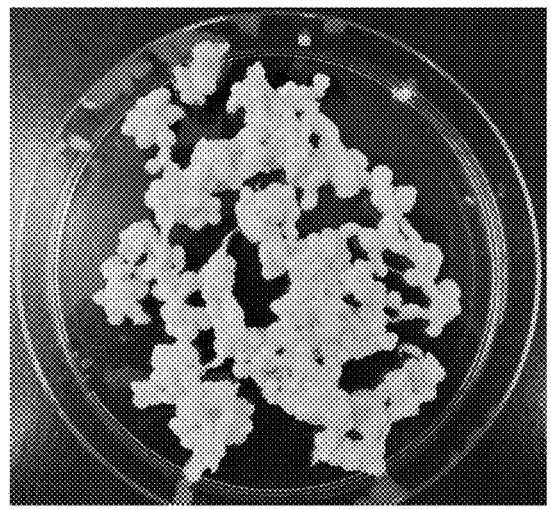
FIG. 13 is a photograph of the gel obtained following the process of WO2008/076975 but using a weight ratio soybean protein/$Ca^{2+}$ of 35:1 (w/w) according to the invention, and using (a) alginate; (b) chitosan; before lyophilization, ground and sieved.
Figure 13:
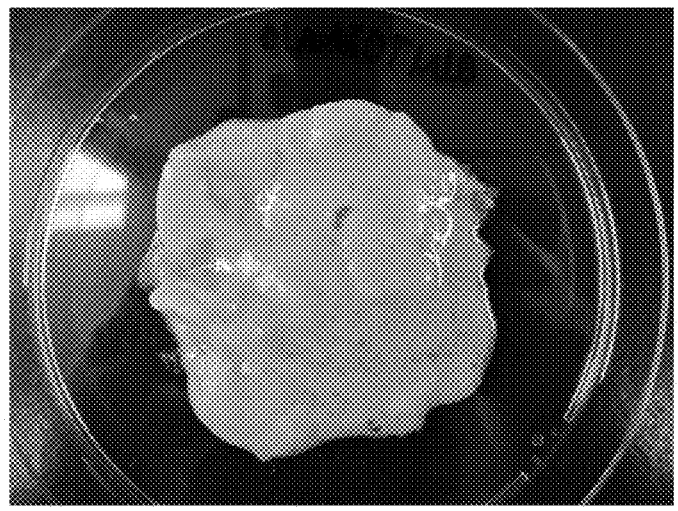
Figure 14:
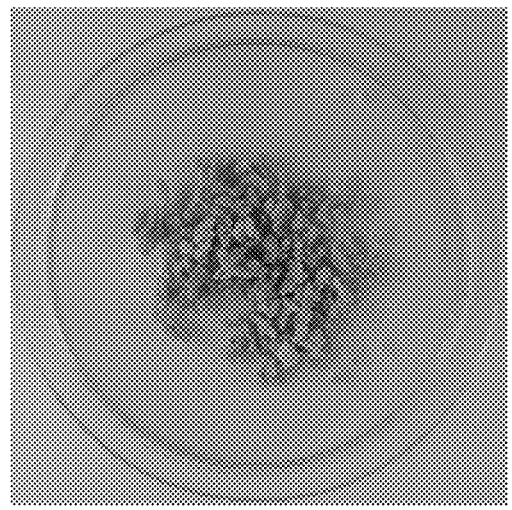
FIG. 14 is a photograph of the gel obtained following the process of WO2008/076975 but using a weight ratio soybean protein/$Ca^{2+}$ of 35:1 (w/w) according to the invention, using (a) alginate; (b) chitosan; after lyophilization and before ground and sieved.
Figure 14:
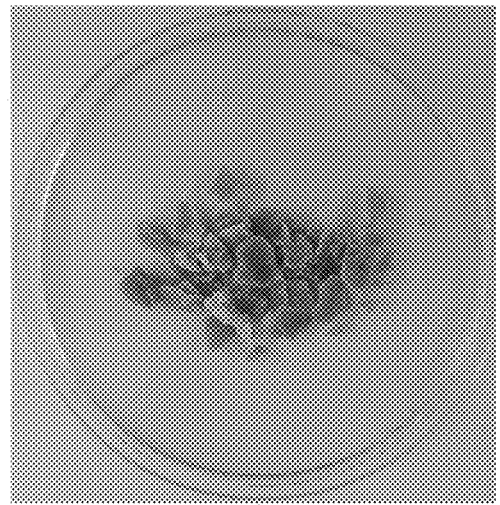

According to this method, the mixture of the different components provides a firmly texture gel, either using alginate or chitosan as constituent of the gel composition (see FIGS. 13 and 14).

Thus, contrary to the method of the present invention where microparticles are spontaneously formed upon mixture of the different components, the process described in WO2008/076975 requires additional steps to obtain a micro-sized structures from the gel previously formed. In fact, the gel needs to be subjected to a lyophilization process and subsequently to grind and sieve in order to obtain solid microsized structures containing soybean protein, bacteria and $Ca^{2+}$.

Figure 15:
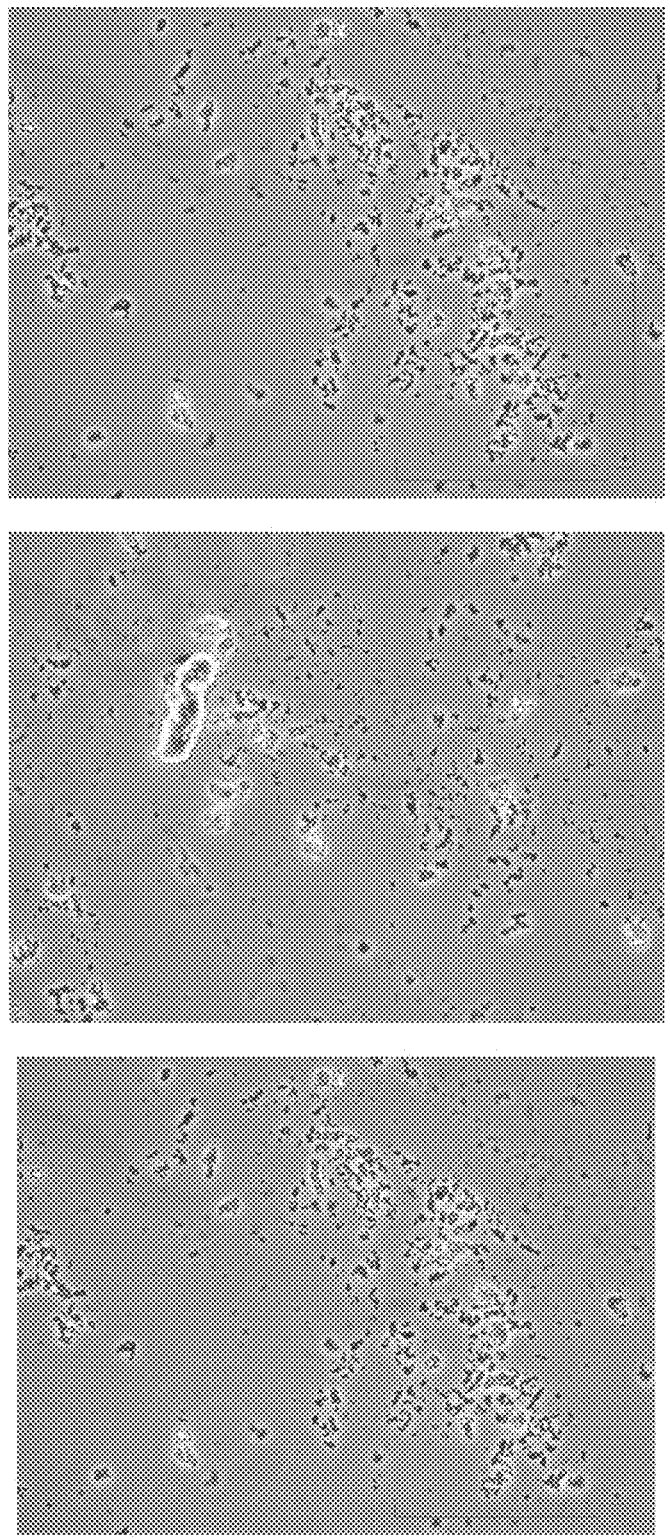
FIG. 15 shows different optical microscopy images of dried, ground and sieved gel obtained following the process of WO2008/076975 but using a weight ratio soybean protein/$Ca^{2+}$ of 35:1 (w/w) according to the invention.

Moreover, as derivable from FIG. 15, the solid structures are not spherical particles as the microparticles obtained from the process of the invention, but irregular crystals or little pieces of gel with a different molecular rearrangement. These microsized structures cannot be considered in any case as self-assembling microparticles such as those obtained from the process of the invention which are spontaneously formed by means of local interactions upon mixture of the bacteria suspension with the soybean protein dispersion in the presence of $Ca^{2+}$.

Finally, the microparticles obtained after the drying process in both sections showed cell viabilities under the LOQ (Limit of Quantification) for the plate count method, far from those obtained from the process of the present invention.

The invention claimed is:

1. A self-assembling matrix-type microparticle comprising a solid matrix and probiotic bacteria, wherein the solid matrix comprises soybean protein and a di- or tri-valent metal cation, in a weight ratio ranging from 1:1 to 40:1, said soybean protein and di- or tri-valent metal cation forming a continuous structure resulting from local interactions between both components, and wherein the probiotic bacteria are entrapped throughout the solid matrix.

2. The self-assembling microparticle according to claim 1, wherein the solid matrix is devoid of any coating material.

3. The self-assembling microparticle according to claim 1, wherein its mean size ranges from 1 to 30 μm.

4. The self-assembling microparticle according to claim 1, wherein the soybean protein is obtained from soybean flour.

5. The self-assembling microparticle according to claim 1, wherein the divalent metal cation is selected from $Ca^{2+}$, $Mg^{2+}$, $Zn^{2+}$, $Fe^{2+}$ and combinations thereof.

6. The self-assembling microparticle according to claim 1, wherein the probiotic bacteria are bacteria of the genus *Bifidobacterium* or *Lactobacillus*.

7. A process for preparing a self-assembling microparticle according to claim 1, said process comprises:
 a) preparing a dispersion of soybean protein in an alkaline aqueous solution;
 b) preparing a suspension of probiotic bacteria;
 c) mixing the suspension of the probiotic bacteria prepared in step b) with the dispersion of soybean protein prepared in step a);
 d) adding to the resulting mixture obtained in step c) a di-valent or tri-valent metal cation, wherein the soybean protein/di- or tri-valent metal cation weight ratio ranges from 1:1 to 40:1.

8. The process according to claim 7, which further comprises drying the microparticles once they are formed.

9. A composition comprising at least one self-assembling microparticle as defined in claim 1.

10. The composition according to claim 9 further comprising a food, pharmaceutical, cosmeceutical or nutraceutical acceptable carrier.

11. The composition according to claim 9, wherein the microparticles are in the form of a dry powder.

12. A food, pharmaceutical, cosmeceutical or nutraceutical product comprising at least one self-assembling microparticle as defined in claim 1.

13. The self-assembling microparticle according to claim 1, having a uniform and a spherical shape.

14. The self-assembling microparticle according to claim 1, further comprising a saccharide, wherein the saccharide does not form part of the solid matrix.

15. A self-assembling matrix-type microparticle comprising a solid matrix and probiotic bacteria, wherein the solid matrix comprises soybean protein and a di- or tri-valent metal cation, in a weight ratio ranging from 1:1 to 40:1, said soybean protein and di- or tri-valent metal cation forming a continuous structure resulting from local interactions between both components, and wherein the probiotic bacteria are entrapped throughout the solid matrix; wherein the microparticle is obtainable by coacervation.

* * * * *